United States Patent
Ozcan et al.

(10) Patent No.: US 9,730,985 B2
(45) Date of Patent: Aug. 15, 2017

(54) METHOD FOR REDUCING BLOOD GLUCOSE

(71) Applicant: The Children's Medical Center Corporation, Boston, MA (US)

(72) Inventors: Umut Ozcan, Jamaica Plains, MA (US); Jaemin Lee, Brookline, MA (US)

(73) Assignee: The Children's Medical Center Corporation, Boston, MA (US)

(*) Notice: Subject to any disclaimer, the term of this patent is extended or adjusted under 35 U.S.C. 154(b) by 0 days.

(21) Appl. No.: 14/885,626

(22) Filed: Oct. 16, 2015

(65) Prior Publication Data

US 2016/0101159 A1 Apr. 14, 2016

Related U.S. Application Data

(62) Division of application No. 14/342,432, filed as application No. PCT/US2012/053096 on Aug. 30, 2012, now Pat. No. 9,186,393.

(60) Provisional application No. 61/530,787, filed on Sep. 2, 2011.

(51) Int. Cl.
| | |
|---|---|
| A61K 38/45 | (2006.01) |
| A61K 31/66 | (2006.01) |
| G01N 33/573 | (2006.01) |
| G01N 33/50 | (2006.01) |

(52) U.S. Cl.
CPC .............. *A61K 38/45* (2013.01); *A61K 31/66* (2013.01); *G01N 33/502* (2013.01); *G01N 33/573* (2013.01); *C12Y 207/12002* (2013.01); *G01N 2333/4703* (2013.01); *G01N 2440/14* (2013.01); *G01N 2800/042* (2013.01)

(58) Field of Classification Search
None
See application file for complete search history.

(56) References Cited

U.S. PATENT DOCUMENTS

| | | | | |
|---|---|---|---|---|
| 2004/0170622 A1* | 9/2004 | Glimcher | ............... | C07K 14/47 424/130.1 |
| 2006/0019910 A1 | 1/2006 | Greenberg | | |
| 2006/0063187 A1* | 3/2006 | Hotamisligil | .......... | A61K 31/13 435/6.11 |
| 2006/0073213 A1* | 4/2006 | Hotamisligil | .......... | A61K 31/13 424/600 |
| 2006/0111436 A1 | 5/2006 | Griffin | | |
| 2009/0203605 A1* | 8/2009 | Segatori | ............. | A61K 31/7088 514/20.1 |
| 2011/0136108 A1* | 6/2011 | Kwon | .................... | C07K 14/47 435/6.1 |
| 2011/0183899 A1* | 7/2011 | Ozcan | ................ | A61K 38/2264 514/5.3 |
| 2012/0202751 A1* | 8/2012 | Koong | ............... | A01K 67/0275 514/20.1 |
| 2014/0088148 A1* | 3/2014 | Dakshanamurthy | . | C07D 213/32 514/333 |
| 2015/0011575 A1* | 1/2015 | Walter | ................. | A61K 31/497 514/275 |

OTHER PUBLICATIONS

Zhou Y. et al. Regulation of Glucose Homeostasis Through a XBP-1 Fox01 Interaction. Nature Medicine 17(3)356-366, Mar. 2011.*
Ueki K. et al. The Other Sweet Face of XBP-1. Nature Medicine 17(3)246-248, Mar. 2011.*
Cuadrado A. et al. Mechanisms and Functions of p38 MAPK Signalling. Biochem J 429:403-417, 2010.*
Lee J. et al. p38 MAPK Mediated Regulation of Xbp1 is Crucial for Glucose Homeostasis. Nature Med 17(10)1251-1261, Oct. 2011.*
Ozcan U. et al. Endoplasmic Reticulum Stress Links Obesity, Insulin Action, and Type 2 Diabetes. Science 306(5695)457-461, Oct. 15, 2004.*
Cuadrado, et al., "Mechanisms and functions of p38 MAOX signaling", Biochem J., 180(3):403-17 (2010).
Bernales, et al., "Intracellular signalling by the unfolded protein response", Annu Rev Cell Dev Biol., 22:487-508 (2006).
Bjork, "The cost of diabetes and diabetes care", Diabetes Res Clin Pract., 54 Suppl 1:S13-8 (2001).
Brancho, et al., "Mechanism of p38 MAP kinase activation in vivo", Genes Dev., 17:1969-78 (2003).
Calfon, et al., "IRE1 couples endoplasmic reticulum load to secretory capacity by processing the XBP-1 mRNA", Nature, 415:92-6 (2002).
Clark, et al., "Post-transcriptional gene regulation by MAP kinases via AU-rich elements" Front Biosci., 14:847-71 (2009).
Clauss, et al., "The basic domain/leucine zipper protein hXBP-1 preferentially binds to and transactivates CRE-like sequences containing an ACGT core", Nucleic Acids Res., 24:1855-64 (1996).
Cox, et al., "Transcriptional induction of genes encoding endoplasmic reticulum resident proteins requires a transmembrane protein kinase", Cell, 73:1197-1206 (1993).
Fagone, et al., Phospholipid biosynthesis program underlying membrane expansion during B-lymphocyte differentiation, J Biol Chem., 282(10):7591-605 (2007).
Kaser, et al., "XBP1 links ER stress to intestinal inflammation and confers genetic risk for human inflammatory bowel disease", Cell, 134:743-56 (2008).
Koong, et al., "Targeting XBP-1 as a novel anti-cancer strategy", Cancer Biol. Ther., 5: 756-9 (2006).

(Continued)

*Primary Examiner* — Ralph Gitomer
(74) *Attorney, Agent, or Firm* — Pabst Patent Group LLP

(57) ABSTRACT

A method of reducing blood glucose in a subject has been developed. In preferred embodiments, the method involves administering to the subject a specific activator of endogenous mitogen-activated protein kinase kinase 6 (MKK3), mitogen-activated protein kinase kinase 6 (MKK4), mitogen-activated protein kinase kinase 6 (MKK6), p38 mitogen-activated protein kinase (p38MAPK), mitogen-activated kinase-activated protein kinase 2 (MK2), or a combination thereof, in an effective amount to reduce blood glucose in a subject. In other embodiments, the method involves administering to the subject a specific activator to increase X-box binding protein 1 (XBP1) phosphorylation on Thr48 and Ser61 in an effective amount to reduce blood glucose in the subject. Methods of identifying agents for reducing blood glucose in a subject are also provided.

6 Claims, 27 Drawing Sheets

(56) References Cited

OTHER PUBLICATIONS

Lee, et al., "XBP-1 regulates a subset of endoplasmic reticulum resident chaperone genes in the unfolded protein response", Mol Cell Biol., 23:7448-59 (2003).
Lee, et al., "Regulation of hepatic lipogenesis by the transcription factor XBP1", Science, 320:1492-6 (2008).
Lee, et al., "IRE1-mediated unconventional mRNA splicing and S2P-mediated ATF6 cleavage merge to regulate XBP1 in signaling the unfolded protein response", Genes Dev., 16:452-66 (2002).
Lee, et al., "p38 MAPK-mediated regulation of Xbp1s is crucial for glucose homeostasis", Nature Med., 17(10):1251-61 (2011).
Lei, et al., "The Bax subfamily of Bcl2-related proteins is essential for apoptotic signal transduction by c-Jun NH(2)-terminal kinase", Mol Cell Biol., 22:4929-42 (2002).
Marciniak and Ron, "Endoplasmic reticulum stress signaling in disease", Physiol Rev., 86:1133-49 (2006).
Martinon, et al., "TLR activation of the transcription factor XBP1 regulates innate immune responses in macrophages", Nature Immunology., 11:411-8 (2010).
Mori, et al., "A transmembrane protein with a cdc2+/CDC28-related kinase activity is required for signalling from the ER to the nucleus", Cell, 74:743-56 (1993).
Nakatani, et al., "Involvement of endoplasmic reticulum stress in insulin resistance and diabetes", J Biol Chem., 280:847-51 (2005).
Narayan, et al., "Lifetime risk for diabetes mellitus in the United States", Jama, 290:1884-90 (2003).
Ozawa, et al., "The endoplasmic reticulum chaperone improves Insulin resistance in type 2 diabetes", Diabetes, 54:657-63 (2005).
Ozcan, et al., "Endoplasmic reticulum stress plays a central role in development of leptin resistance", Cell metabolism, 9:35-51 (2009).
Ozcan, et al., "Loss of the tuberous sclerosis complex tumor suppressors triggers the unfolded protein response to regulate insulin signalling and apoptosis", Mol. Cell., 29:541-51(2006).
Ozcan, et al., "Endoplasmic reticulum stress links obesity, insulin action, and type 2 diabetes", Science, 306:457-61 (2004).
Ozcan, et al., "Chemical chaperones reduce ER stress and restore glucose homeostasis in a mouse model of type 2 diabetes", Science, 313:1137-40 (2006).
Park, et al., Dietary and genetic obesity promote liver inflammation and tumorigenesis by enhancing IL-6 and TNF expression Cell, 140:197-208 (2010a).
Park, et al., "The regulatory subunits of PI3K, p85alpha and p85beta, interact with XBP-1 and increase its nuclear translocation", Nature Med., 16:429-37 (2010b).
Raingeaud, et al., "MKK3- and MKK6-regulated gene expression is mediated by the p38 mitogen-activated protein kinase signal transduction pathway", Mol Cell Biol., 16:1247-55 (1996).
Richardson, et al., "An essential role for XBP-1 in host protection against immune activation in C. elegans", Nature, 463:1092-5 (2010).
Ron and Walter, "Signal integration in the endoplasmic reticulum unfolded protein response", Nat Rev Mol Cell Biol., 8:519-29 (2007).
Sado, et al., "Protective effect against Parkinson's disease-related insults through the activation of XBP1", Brain Res, 1257:16-24 (2009).
Schaeffer and Weber, "Mitogen-activated protein kinases: specific messages from ubiquitous messengers", Mol Cell Biol., 19:2435-44 (1999).
Schroder and Kaufman, "The mammalian unfolded protein response", Annu Rev Biochem., 74:739-69 (2005).
Sriburi, et al., "XBP1: a link between the unfolded protein response, lipid biosynthesis and biogenesis of the endoplasmic reticulum", J Cell Biol., 167:35-41 (2004).
Sriburi, et al., "Coordinate regulation of phospholipid biosynthesis and secretory pathway gene expression in XBP-1(S)-induced endoplamic reticulum biogenesis", J Biol Chem., 282(10):7024-34 (2007).
Sun, "MAPKs and metabolic disease", annual report 2010, National resouce center for mutant mice model animal research center of Najing University MOE key laboratory of model animal for disease study, Nanjing Biomedical Research Institute, http://www.nice-mice.cn/pdf/MARC2010.pdf>, pp. 22-23 retrieved from the internet Jan. 23, 2013.
Tournier, et al., "MKK7 is an essential component of the JNK signal transduction pathway activated by proinflammatory cytokines", Genes Dev., 15:1419-26 (2001).
Yoshida, et al., "XBP1 mRNA is induced by ATF6 and spliced by IRE1 in response to ER stress to produce a highly active transcription factor", Cell, 107:881-91 (2001).
Yustein, et al., "Comparative studies of a new subfamily of human Ste20-like kinases; homodimerization, subcellular localization, and selective activation of MKK3 and p38", Oncogene, 22:6129-41 (2003).
Zhou, et al., "Regulation of glucose homeostasis through a XBP-1-FoxO1 interaction", Nature Med., 17(3):356-65 (2011).

* cited by examiner

METHOD FOR REDUCING BLOOD GLUCOSE

CROSS REFERENCE TO RELATED APPLICATIONS

This application is a divisional of U.S. Ser. No. 14/342,432, filed Mar. 3, 2014, now U.S. Pat. No. 9,186,393, which is a 0371 application of PCT/US2012/053096, filed in the United States Receiving Office for the PCT on Aug. 30, 2012, which claims the benefit of and priority to U.S. Provisional Application No. 61/530,787 filed in the United States Patent and Trademark Office on Sep. 2, 2011, each of which is incorporated by reference herein in its entirety.

STATEMENT REGARDING FEDERALLY SPONSORED RESEARCH OR DEVELOPMENT

This invention was made with government support under Agreement R01DK081009 awarded by the National Institutes of Health. The government has certain rights in the invention.

REFERENCE TO SEQUENCE LISTING

The Sequence Listing submitted as a text file named "CMCC_2291_PCT_ST25.txt," created on Sep. 4, 2012, and having a size of 10,835 bytes is hereby incorporated by reference pursuant to 37 C.F.R. § 1.52(e)(5).

FIELD OF THE INVENTION

The invention is generally related to the field of metabolic homeostasis and insulin resistance, more particularly to methods and compositions for reducing endoplasmic reticulum stress, lowering blood glucose levels, and treating type II diabetes and obesity.

BACKGROUND OF THE INVENTION

For individuals born in the United States in the year 2000, the estimated lifetime risk for developing diabetes is 32.8% for males and 38.5% for females, with Hispanic Americans having estimated life time risks for diabetes of approximately 50% (Narayan, K. M., et al. *Jama* (2003) 290:1884-1890). Diabetes is the leading cause of adult blindness and accounts for over 40% of the new cases of end-stage renal disease. The risk of heart disease and stroke is two to four times higher, and the risk of lower extremity amputation is approximately 20 times higher, for people with diabetes than for those without the disease (Bjork, S. (2001) *Diabetes Res Clin Pract* 54 Suppl 1:S13-18). Despite its enormous burden on human health and on the global economy, few significant advances have been made over the last three decades in the therapeutic treatment of type 2 diabetes. Moreover, despite intense research efforts, the link between obesity and type 2 diabetes is not well understood.

There is an urgent need for effective treatments to reduce ER stress and/or lower blood glucose levels in obese and/or type II diabetic individuals.

Therefore, it is an object of the invention to provide compositions and methods for reducing ER stress in obese and/or type II diabetic individuals.

It is a further object of the invention to provide compositions and methods for lowering blood glucose levels in obese and/or type II diabetic individuals.

SUMMARY OF THE INVENTION

Compositions and methods for reducing blood glucose in a subject have been developed. These methods involve increasing p38 MAPK activity in the liver of obese and diabetic mice in order to significantly increase X-box binding protein 1 (XBP1) phosphorylation and nuclear translocation, which markedly enhances glucose tolerance. Prior to this observation, the general view in the obesity and diabetes field was that stress-activated protein kinase (SAPK) signaling is detrimental to metabolic homeostasis.

In some embodiments, the method involves administering to the subject a specific activator of endogenous mitogen-activated protein kinase kinase 3 (MKK3), mitogen-activated protein kinase kinase 4 (MKK4), mitogen-activated protein kinase kinase 6 (MKK6), p38 mitogen-activated protein kinase (p38MAPK), mitogen-activated kinase-activated protein kinase 2 (MK2), or a combination thereof, in an effective amount to reduce blood glucose in the subject. In other embodiments, the method involves administering to the subject a specific activator of X-box binding protein 1 (XBP1) in an effective amount to reduce blood glucose in the subject, wherein the specific activator increases phosphorylation of XBP1 on Thr48 and Ser61.

Obesity can lead to endoplasmic reticulum (ER) stress, which in turn contributes to the development of insulin resistance and type-2 diabetes and increased blood glucose levels. Therefore, in preferred embodiments, the subject is obese. In some embodiments, the subject has type-2 diabetes or pre-diabetes.

MKK3 is generally activated by phosphorylation at residue Ser189. Therefore, in some embodiments the activator of MKK3 promotes phosphorylation of MKK3 at residue Ser189. MKK4 is generally activated by phosphorylation at residues Ser257 and Thr261. Therefore, in some embodiments the activator of MKK4 promotes phosphorylation of MKK4 at residues Ser257, Thr261, or a combination thereof. MKK6 is generally activated by phosphorylation at residues Ser207 and Thr211. Therefore, in some embodiments the activator of MKK6 promotes phosphorylation of MKK6 at residues Ser207, Thr211, or a combination thereof. p38MAPK is generally activated by phosphorylation at residues Thr180 and Tyr182. Therefore, in some embodiments the activator of p38MAPK promotes phosphorylation of p38MAPK at residues Thr180, Tyr182, or a combination thereof. MK2 is generally activated by phosphorylation at residue T334. Therefore, in some embodiments the activator of MK2 promotes phosphorylation of MK2 at residues T334. In other embodiments, the specific activator of MKK6, p38MAPK, MK2, or a combination thereof, is an allosteric activator.

The pharmaceutical composition is preferably administered at a non-toxic dosage, wherein an effective amount is maintained in the subject's blood for a period of at least 5, 6, 7, 8, 9, 10, or more days. For example, in some embodiments, the pharmaceutical composition is an extended release formulation.

Screening systems and methods for identifying an agent that reduces blood glucose in a subject are also provided. In some embodiments, the method involves contacting a sample containing X-box binding protein 1 (XBP1) with a candidate agent and detecting phosphorylation of XBP1, wherein an increase in XBP1 phosphorylation (e.g., at residues Thr48, Ser61, or a combination thereof) compared to a control identifies a candidate agent for reducing blood glucose in a subject. In other embodiments, the method involves contacting a sample containing XBP1 with a candidate agent and detecting cellular localization of XBP1, wherein an increase in XBP1 nuclear translocation compared to a control identifies an agent for reducing blood glucose in a subject. In still other embodiments, the method involves contacting a sample containing p38MAPK with a candidate agent and detecting phosphorylation of p38MAPK, wherein an increase in p38MAPK phosphorylation (e.g., Thr180, Tyr182, or a combination thereof) compared to a control identifies an agent for reducing blood glucose. In still other embodiments, the method involves contacting a sample containing MK2 with a candidate agent and detecting phosphorylation of MK2, wherein an increase in MK2 phosphorylation (e.g., TT334) compared to a control identifies an agent for reducing blood glucose.

DETAILED DESCRIPTION OF THE INVENTION

I. Definitions

Figure 1:
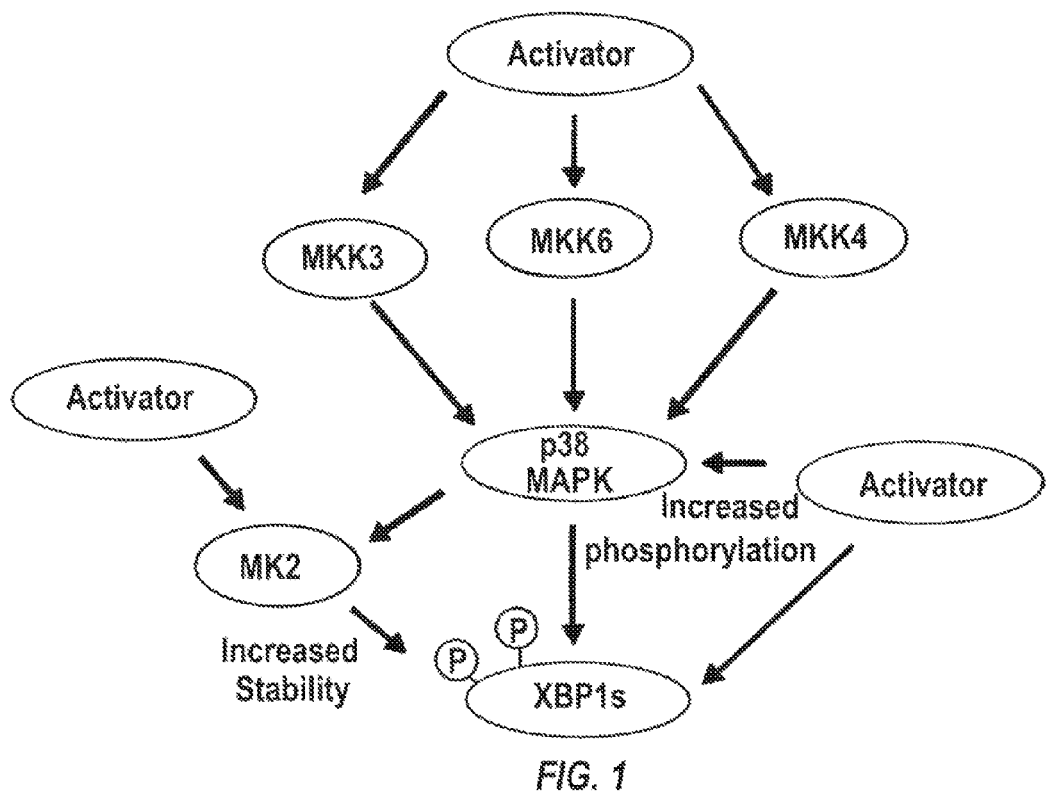
FIG. 1 is a diagram illustrating targets of activation that can promote XBP1 phosphorylation and nuclear translocation, which markedly enhances glucose tolerance.

The term "subject" or "patient" refers to any individual who is the target of administration. The term includes human and veterinary subjects and does not denote a particular age or sex.

The term "effective amount" refers to a sufficient amount of an agent to provide a desired effect. The exact amount required will vary from subject to subject, depending on the species, age, and general condition of the subject, the severity of disease that is being treated, the particular agent used, and its mode of administration. An appropriate "effective amount" may be determined empirically by one of ordinary skill in the art using routine methods.

The term "treatment" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "specific activator" as used herein refers to an agent that binds and activates endogenous target proteins but does not bind or affect the activity of other (non-target) proteins at detectable levels.

The term "allosteric" refers to the ability of an agent to regulate an enzyme's activity by binding at a site (i.e., allosteric site) other than the enzyme's active site (i.e., orthosteric site). Effectors that enhance the enzyme's activity are referred to as allosteric activators. Allosteric activation occurs when the binding of the agent enhances the attraction between the enzyme and its substrate.

The term "kinase" refers to an enzyme that modifies other proteins by chemically adding phosphate groups to them (phosphorylation). The term includes natural and synthetic proteins and peptidomimetics.

The term "phosphatases" refers to an enzyme that removes a phosphate group from its substrate by hydrolysing phosphoric acid monoesters into a phosphate ion and a molecule with a free hydroxyl group. The term includes natural and synthetic proteins and peptidomimetics.

The term "peptidomimetic" refers to non-natural molecules that mimic peptide structures. They typically arise either from modification of an existing peptide, or by synthesizing compounds that mimic peptides, such as peptoids and β-peptides. Modifications include altered backbones and the incorporation of nonnatural amino acids. The altered chemical structure is designed to advantageously adjust the molecular properties such as, stability or biological activity.

The term "promote" refers to a detectable increase in activity, levels, response, condition, or other biological parameter. This includes, for example, an increase of at least 5%, 10%, 20%, 30%, 40%, 50%, 60%, 70%, 80%, 90%, 100%, or any amount in between, in the activity, levels, response, or condition as compared to the native or control level.

The term "reduce" means to a detectable decrease in activity, levels, response, condition, or other biological parameter. This includes, for example, a decrease of at least 5%, 10%, 20%, 30%, 40%, 50%, 60%, 70%, 80%, 90%, 100%, or any amount in between, when compared to the native or control level.

The term "glucose homeostasis" refers to the balance of insulin and glucagon to maintain blood glucose levels within normal levels (i.e about 64.8 to 104.4 mg/dl). An agent that "promotes glucose hemostasis" preferably reduces blood glucose levels down to, but not below, normal levels.

The term "glycogenolysis" refers to the conversion of glycogen polymers to glucose monomers.

The term "gluconeogenesis" refers to the generation of glucose from non-carbohydrate carbon substrates such as lactate, glycerol, and glucogenic amino acids.

The term "insulin sensitivity" refers to the amount of insulin needed to lower blood sugar in a subject.

The term "insulin resistance" refers a physiological condition in a subject where insulin becomes less effective at lowering blood sugars (low insulin sensitivity), which results in an increase in blood glucose. Insulin resistance in muscle and fat cells reduces glucose uptake, whereas insulin resistance in liver cells results in reduced glycogen synthesis and storage and a failure to suppress glucose production and release into the blood.

The term "type-2 diabetes," "non-insulin-dependent diabetes mellitus (NIDDM)," and "adult-onset diabetes" refer to a metabolic disorder characterized by insulin resistance and high blood glucose (e.g., fasting plasma glucose ≥7.0 mmol/l (126 mg/dl)).

The term "pre-diabetes" refers to a condition that occurs when a person's blood glucose levels are higher than normal but not high enough for a diagnosis of type 2 diabetes.

The term "endoplasmic reticulum (ER) stress" and "unfolded protein response (UPR)" refer to a cellular stress response to an accumulation of unfolded or misfolded proteins in the lumen of the endoplasmic reticulum. The UPR attempts to restore normal function of the cell by halting protein translation and activate the signaling pathways that lead to increasing the production of molecular chaperones involved in protein folding. However, in conditions of prolonged stress, the goal of the UPR changes from being one that promotes cellular survival to one that commits the cell to a pathway of apoptosis. ER stress has also been shown to link obesity with insulin resistance and type 2 diabetes.

The term "obese" refers to a medical condition in which excess body fat has accumulated to the extent that it may have an adverse effect on health, leading to reduced life expectancy and/or increased health problems. A person is generally considered obese if their body mass index (BMI) is greater than 30 kg/m$^2$ and overweight (pre-obese) if their BMI is between 25 and 30 kg/m$^2$.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

II. Compositions

The endoplasmic reticulum (ER) is responsible for the synthesis of secretory and membrane proteins, which acquire their lowest energy three-dimensional structures within this organelle. In addition to protein synthesis, the ER also plays a key role in lipid and cholesterol biosynthesis. Perturbations of ER homeostasis due to viral infections, accumulation of unfolded proteins and reduction in the cellular energy levels, or alterations in the capacity of the ER to cope with increasing demand for protein synthesis, can create a condition referred to as ER stress, and lead to activation of a group of complex signaling pathways, called the unfolded protein response (UPR) (Marciniak, S. J. & Ron, D. (2006) *Physiol Rev* 86:1133-1149; Schroder, M. & Kaufman, R. J. (2005) *Annu Rev Biochem* 74:739-789; Ron, D. & Walter, P. (2007) *Nat Rev Mol Cell Biol* 8:519-529; Bernales, S., et al. (2006) *Annu Rev Cell Dev Biol* 22:487-508). Two type-I transmembrane kinases (the PKR-like endoplasmic reticulum kinase (PERK) and the inositol requiring enzyme-1 (IRE1)), plus a specific type-II transmembrane protein (the activating transcription factor-6 (ATF6)), have major roles in initiating UPR signaling. PERK phosphorylates the eukaryotic translation initiation factor 2 alpha (eIF2α) at Ser51 and leads to a global attenuation in the initiation of translation, while proteolytic cleavage of ATF6 and its translocation to the nucleus increase the expression of genes that are important in protein folding and ER homeostasis (Mareiniak, S. J. & Ron, D. (2006) *Physiol Rev* 86:1133-1149; Schroder, M. & Kaufman, R. J. (2005) *Annu Rev Biochem* 74:739-789; Ron, D. & Walter, P. (2007) *Nat Rev Mol Cell Biol* 8:519-529; Bernales, S., et al. (2006) *Annu Rev Cell Dev Biol* 22:487-508).

Of these three transmembrane proteins, IRE1 is the most conserved evolutionarily. In addition to its kinase activity, IRE1 also has endoribonuclease activity (Cox, J. S., et al. (1993) *Cell* 73:1197-1206; Mori, K., et al. (1993) *Cell* 74:743-756). The endoribonuclease domain of IRE1 cleaves the mRNA of X-Box Binding Protein-1 (XBP1), which is the mammalian homolog of yeast Hac1p (Yoshida, H., et al. (2001) *Cell* 107:881-891; Lee, K., et al. (2002) *Genes Dev* 16:452-466; Calfon, M., et al. (2002) *Nature* 415:92-96). XBP1 belongs to the CREB/ATF family of transcription factors and is a basic region-leucine zipper transcription factor (Clauss, I. M., et al. (1996) *Nucleic Acids Res* 24:1855-1864). IRE1 cleaves the full length XBP1 mRNA to initiate removal of a 26 bp intron, converting the 267 amino acid unspliced XBP1 protein (XBP1u) to the highly active 371 amino acid spliced. XBP1 (XBP1s), a transcription factor that functions as a master regulator of ER folding capacity (Marciniak, Si. & Ron, D. (2006) *Physiol Rev* 86:1133-1149; Schroder, M. & Kaufman, R. J. (2005) *Annu Rev Biochem* 74:739-789; Ron, D. & Walter, P. (2007) *Nat Rev Mol Cell Biol* 8:519-529; Bernales, S., et al. (2006) *Annu Rev Cell Dev Biol* 22:487-508). Migration of XBP1s to the nucleus leads to upregulation of gene expression of ER chaperones (Lee, A. H., et al. (2003) *Mol Cell Biol* 23:7448-7459; Sriburi, R., et al. (2004) *J Cell Biol* 167:35-41) and of the components of ER-associated degradation (ERAD). XBP1s also plays a key role in ER expansion (Sriburi, R., et al. (2007) *J Biol Chem* 282(10):7024-34; Fagone, P., et al. (2007) *J Biol Chem* 282(10):7591-605).

XBP1s is linked to a number of diseases, including insulin resistance and type 2 diabetes (Ozcan, U., et al. (2008) *Mol Cell* 29:541-551; Ozcan, U., et al. (2006) *Science* 313:1137-1140; Ozcan, U., et al. (2004) *Science* 306:457-461), leptin resistance and obesity (Ozcan, L., et al. (2009) *Cell metabolism* 9:35-51), inflammation (Richardson, C. E., et al. (2010) *Nature* 463:1092-1095; Martinon, F., et al. (2010) *Nature immunology* 11:411-418), fatty liver disease (Lee, A. H., et al. (2008) *Science* 320:1492-1496), neurodegeneration (Sado, M., et al. (2009) *Brain research* 1257:16-24), inflammatory bowel disease (IBD) (Kaser, A., et al. (2008) *Cell* 134:743-756) and cancer (Koong, A. C., et al. (2006) *Cancer Biol Ther* 5: 756-759). It is also involved in the regulation of a variety of cellular processes (Ron, D. & Walter, P. (2007) *Nat Rev Mal Cell Biol* 8:519-529; Bernales, S., et al. (2006) *Annu Rev Cell Dev Biol* 22:487-508).

Obesity leads to the development of ER stress and activates the UPR in the liver, adipose tissue and brain (Ozcan, U., et al. (2008) *Mol Cell* 29:541-551; Ozcan, U., et al. (2006) *Science* 313:1137-1140; Ozcan, U., et al. (2004) *Science* 306:457-461; Ozcan, L., et al. (2009) *Cell metabolism* 9:35-51; Nakatani, Y., et al. (2005) *J Biol Chem* 280:847-851; Ozawa, K., et al. (2005) *Diabetes* 54:657-663), in turn contributing to the development of insulin resistance, type-2 diabetes and leptin resistance. Reversal of ER stress with chemical chaperones increases both insulin and leptin sensitivity (Ozcan, U., et al. (2006) *Science* 313:1137-1140, Ozcan, L., et al. (2009) *Cell metabolism* 9:35-51).

Nuclear translocation of XBP1s is severely reduced under conditions of obesity, due to loss of interactions between XBP1s and the p85 regulatory subunits (Park, S. W., et al. (2010) *Nature Med* 16:429-437). Obesity creates an XBP1-deficient condition in the liver. If XBP1s is reactivated in the liver by forced ectopic expression in severely obese and diabetic mice, blood glucose levels are reduced to euglycemia (Zhou, Y., et al. (2011) *Nature Med* 17(3):356-65). Thus, unraveling the networks that regulate XBP1s activity has the strong potential to reveal unique approaches for the treatment of obesity, type 2 diabetes, and other XBP1s-associated diseases.

XBP1s also interacts with the Forkhead box O1 (FoxO1) transcription factor and directs it toward proteasome-mediated degradation. XBP-1s, through its interaction with FoxO1, can bypass hepatic insulin resistance independent of its effects on ER folding capacity.

A. Specific Activators

Specific activators of MKK3, MKK4, MKK6, p38 MAPK, and/or MK2 can reduce blood glucose levels in a subject. In preferred embodiments, the specific activator is a small molecule.

Mitogen-activated protein kinase kinase 3 (MKK3), also known as mitogen-activated protein kinase kinase 3 and MAP kinase kinase 3 (MAPKK 3), is an enzyme that in humans is encoded by the MAP2K3 gene, on chromosome 17. This protein phosphorylates and activates p38 mitogen-activated protein kinases (p38 MAPK) kinase.

Mitogen-activated protein kinase kinase 6 (MKK4), also known as mitogen-activated protein kinase kinase 4 and MAP kinase kinase 6 (MAPKK 4), is an enzyme that in humans is encoded by the MAP2K4 gene, on chromosome 17. This protein phosphorylates and activates p38 mitogen-activated protein kinases (p38 MAPK) kinase.

Mitogen-activated protein kinase kinase 6 (MKK6), also known as mitogen-activated protein kinase kinase 6 and MAP kinase kinase 6 (MAPKK 6), is an enzyme that in humans is encoded by the MAP2K6 gene, on chromosome 17. This protein phosphorylates and activates p38 mitogen-activated protein kinases (p38 MAPK) kinase in response to inflammatory cytokines or environmental stress.

p38 MAPK is a class of mitogen-activated protein kinases that are responsive to stress stimuli, such as cytokines, ultraviolet irradiation, heat shock, and osmotic shock, and are involved in cell differentiation and apoptosis. Four isoforms of p38 MAPK have been identified: p38-α (MAPK14), p38-β (MAPK11), p38-γ (MAPK12), and p38-δ (MAPK13). p38 MAPK phosphorylates mitogen-activated kinase-activated protein kinase 2 (MK2) and X-box binding protein 1 (XBP1) in liver cells of obese mice.

MK2 is an enzyme that in humans is encoded by the MAPKAPK2 gene. Heat shock protein HSP27 is one of the substrates of this kinase in vivo.

Specific activators of XBP1 that increase phosphorylation on Thr48 and Ser61 can also reduce blood glucose in the subject. XBP1 is a protein which in humans is encoded by the XBP1 gene. The XBP1 gene is located on chromosome 22. The XBP1 protein is a transcription factor that regulates the expression of genes important to the proper functioning of the immune system and in the cellular stress response.

1. Allosteric Activators

Positive allosteric modulation (also known as allosteric activation) generally occurs when the binding of one ligand enhances the binding between an enzyme and its substrate. Under normal circumstances, it acts by causing a conformational change in the enzyme, which results in a change in the binding affinity of the enzyme for its substrate.

There are a number of advantages in using allosteric modulators as preferred therapeutic agents over classic orthosteric ligands. For example, these modulators have a decreased potential for toxic effects, since modulators with limited co-operativity will have a ceiling level to their effect, irrespective of the administered dose. In addition, allosteric modulators are not limited to simply turning a receptor on or off, the way most drugs are. Instead, they act more like a dimmer switch, offering control over the intensity of activation or deactivation, while allowing the body to retain its natural control over initiating receptor activation.

MKK3, MKK4, and MKK6 bind and phosphorylate p38 MAPK. Therefore, in some embodiments, an allosteric activator of MKK3, MKK4, or MKK6 binds MKK3, MKK4, or MKK6 and enhances binding between MKK3, MKK4, or MKK6 kinase domain and p38 MAPK and/or phosphorylation of p38MAPK (e.g., at residues Thr180 and/or Tyr182). p38 MAPK binds and phosphorylates XBP1. Therefore, in some embodiments, an allosteric activator of p38 MAPK binds p38 MAPK and enhances binding between p38 MAPK kinase domain and XBP1 and/or phosphorylation of XBP1 (e.g., at residues Thr48 and/or Ser61).

Allosteric activators of MKK3, MKK4, MKK6, p38 MAPK, and/or MK2 can be identified by first screening compound libraries for compounds that bind MKK3, MKK4, MKK6, p38 MAPK, and/or MK2. These compounds can be further screened to verify that they do not bind MKK3, MKK4, MKK6, p38 MAPK, and/or MK2 at the active (kinase) domain. Candidate compounds can then be screened in cell-based or cell-free assays containing MKK3, MKK4, MKK6, p38 MAPK, and/or MK2 and the appropriate substrates under conditions suitable for substrate phosphorylation. Substrate phosphorylation can be determined directly (e.g., phosphor-specific antibodies) or indirectly (e.g., activity of substrate enzyme).

2. Kinase Activators

MKK3, MKK4, MKK6, p38 MAPK, MK2, and XBP1 are each activated by phosphorylation of amino acid residues by kinases. Therefore, in some embodiments, the specific activator of MKK3, MKK4, MKK6, p38 MAPK, and/or MK2 is a kinase. In some embodiments, the specific activator that increases XBP1 phosphorylation is a kinase.

The kinase can be a naturally occurring protein or variant thereof. Protein variants include peptide fragments, peptidomimetics, and recombinant proteins (including fusion proteins).

For example, MKK3, MKK4, and MKK6 activate p38 MAP kinase by phosphorylation at Thr180 and Tyr182. Therefore, the specific activator of p38 MAPK can be a dual-specific protein kinase having the Enzyme Commission number (EC number) 2.7.12.2. In some embodiments, the specific activator of p38 MAPK is MKK3, MKK4, or MKK6, or a fragment or variant thereof that phosphorylates p38 MAPK. p38 MAP kinase activates XBP1 by phosphorylation at Thr48 and Ser61. In some embodiments, the specific activator of XBP1 is p38 MAP kinase, or a fragment or variant thereof that phosphorylates XBP1. Suitable peptide fragments preferably include at least the kinase domain and protein binding domain of the natural protein.

Kinase activators can also be identified by screening compound libraries. In some embodiments, the library is first screened for compounds that bind MKK3, MKK4, MKK6, p38 MAPK, MK2, or XBP1 at the phosphorylation site(s) and/or displaces a natural kinase from MKK3, MKK4, MKK6, p38 MAPK, MK2, or XBP1. For example, a compound library can be screened for compounds that bind p38 MAPK at Thr180 and/or Tyr182 or for compounds that displace MKK3, MKK4, or MKK6 from p38 MAPK. Alternatively, or in addition, compound libraries, or candidate agents from the prior screen, can be screened for compounds that phosphorylate MKK3, MKK4, MKK6, p38 MAPK, MK2, or XBP1. Compound libraries or candidate agents can also be screened for the ability to activate MKK3, MKK4, MKK6, p38 MAPK, MK2, or XBP1 and induce XBP1 nuclear internalization in vitro or in vivo.

Allosteric and kinase activators identified for use in the disclosed methods are preferably also screened against other map kinase substrates to determine if the compound's activity is specific for MKK3, MKK4, MKK6, p38 MAPK, MK2, or XBP1. Compounds that substantially activate or inhibit other enzymes are non-specific and are more likely to cause side-effects and toxicity. Candidate activators are therefore also preferably tested in vivo for therapeutic effect, side-effects, and toxicity.

3. Peptides and Peptidomimetics

Endogenous MKK3, MKK4, MKK6, p38 MAPK, and/or MK2 activity can also be supplemented using exogenous MKK3, MKK4, MKK6, p38 MAPK, and/or MK2 protein (peptide), or variants thereof that activate target substrate. The peptide or peptidomimetics of MKK3, MKK4, MKK6, p38 MAPK, and/or MK2 can be administered to subjects in a formulation that permits entry of the peptides or peptidomimetics into liver cells of the subject.

a. Peptide Variants

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues.

It is understood that one way to define the variants and derivatives of the disclosed proteins herein is through defining the variants and derivatives in terms of sequence identity to specific known sequences. Specifically disclosed are variants of these and other proteins herein disclosed which have at least 70%, 75%, 80%, 85%, 90% or 95% sequence identity to the endogenous sequence. Those of skill in the art readily understand how to determine the sequence identity of two proteins. For example, the sequence identity can be calculated after aligning the two sequences so that the sequence identity is at its highest level.

b. Peptidomimetics

Peptidomimetics have general features analogous to their parent peptide structures, such as enzyme activity. The peptidomimetic materials can be classified into five categories: α-peptides, β-peptides, γ-peptides, δ-peptides, and oligomers having backbones which can adopt helical or sheet conformations. Copolymers of these peptides can also be used.

Examples of α-peptide peptidomimetics include, but are not limited to, N,N'-linked oligoureas, oligopyrrolinones, oxazolidin-2-ones, azatides and azapeptides. Examples of β-peptides include, but are not limited to, peptide foldamers, aminoxy acids, sulfur-containing peptide analogues, and hydrazino peptides. Examples of γ-peptides include, but are not limited to, peptide foldamers, oligoureas, oligocarbamates, and phosphodiesters. Examples of δ-peptides include, but are not limited to, alkene-based amino acids and carbopeptoids, such as pyranose-based carbopeptoids and furanose-based carbopeptoids.

Another class of compounds includes oligomers having backbones which can adopt helical or sheet conformations. Example of such compounds include, but are not limited to, compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination.

Examples of compounds containing backbones utilizing bipyridine segments include, but are not limited to, oligo (pyridine-pyrimidines), oligo(pyridine-pyrimidines) with hydrazal linkers, and pyridine-pyridazines.

Examples of compounds containing backbones utilizing solvophobic interactions include, but are not limited to, oligoguanidines, aedamers (structures which take advantage of the stacking properties of aromatic electron donor-acceptor interactions of covalently linked subunits) such as oligomers containing 1,4,5,8-naphthalene-tetracarboxylic diimide rings and 1,5-dialkoxynaphthalene rings, and cyclophanes such as substituted N-benzyl phenylpyridinium cyclophanes.

Examples of compounds containing backbones utilizing side chain interactions include, but are not limited to, oligothiophenes such as oligothiophenes with chiral p-phenyl-oxazoline side chains, and oligo(m -phenylene-ethynylene)s.

Examples of compounds containing backbones utilizing hydrogen bonding interactions include, but are not limited to, aromatic amide backbones such as oligo(acylated 2,2'-bipyridine-3,3'-diamine)s and oligo(2,5-bis[2-aminophenyl] pyrazine)s, diaminopyridine backbones templated by cyanurate, and phenylene-pyridine-pyrimidine ethynylene backbones templated by isophthalic acid.

Examples of compounds containing backbones utilizing metal coordination include, but are not limited to, zinc bilinones, oligopyridines complexed with Co(II), Co(III), Cu(II), Ni(II), Pd(II), Cr(III), or Y(III), oligo(m-phenylene ethynylene)s containing metal-coordinating cyano groups, and hexapyrrins.

c. Protein Transduction Domains

The proteins or protein variants can be linked to an internalization sequence or a protein transduction domain to effectively enter the cell. Recent studies have identified several cell penetrating peptides, including the TAT transactivation domain of the HIV virus, antennapedia, and transportan that can readily transport molecules and small peptides across the plasma membrane. Polyarginine has shown an even greater efficiency of transporting peptides and proteins across the plasma, membrane making it an attractive tool for peptide mediated transport. Non-arginine has been described as one of the most efficient polyarginine based protein transduction domains, with maximal uptake of significantly greater than TAT or antennapeadia. Peptide mediated cytotoxicity has also been shown to be less with polyarginine-based internalization sequences. $R_9$ mediated membrane transport is facilitated through heparan sulfate proteoglycan binding and endocytic packaging. Once internalized, heparan is degraded by heparanases, releasing $R_9$ which leaks into the cytoplasm. Studies have recently shown that derivatives of polyarginine can deliver a full length p53 protein to oral cancer cells, suppressing their growth and metastasis, defining polyarginine as a potent cell penetrating peptide.

Thus, the provided polypeptide can contain a cellular internalization transporter or sequence. The cellular internalization sequence can be any internalization sequence known or newly discovered in the art, or conservative variants thereof. Non-limiting examples of cellular internalization transporters and sequences include Polyarginine (e.g., $R_9$), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis -Guanidinium-Spermidine-Cholesterol, and BGTC (Bis-Guanidinium-Tren-Cholesterol)

B. Phosphatase Inhibitors

Another way to increase activity of MKK3, MKK4, MKK6, p38 MAPK, MK2, and/or XBP1 is to inhibit dephosphorylation of the endogenous proteins. Phosphatases are enzymes that remove the phosphate group from substrate proteins that were added by kinases. Therefore, in some embodiments, inhibitors of phosphatases for MKK3, MKK4, MKK6, p38 MAPK, MK2, and/or XBP1 can be used in the disclosed methods to increase MKK3, MKK4, MKK6, p38 MAPK, MK2, and/or XBP1 activity.

For example, protein phosphatase 2A (PP2A) has been shown to dephosphorylate p38 MAPK in some cells. Therefore, in some embodiments, a specific inhibitor of PP2A can increase p38 MAPK activity. Phosphatases that dephosphorylate MKK3, MKK4, MKK6, p38 MAPK, MK2, and/or XBP1 in liver cells of obese subjects can be identified using routine skill. Moreover, specific inhibitors of many phosphatases have been identified and are commercially available.

Phosphatase inhibitors can also be identified by screening compound libraries. As above, in some embodiments, the library is first screened for compounds that bind MKK3, MKK4, MKK6, p38 MAPK, MK2, and/or XBP1 at the phosphorylation site(s) and/or displaces a natural kinase or phosphatase from MKK3, MKK4, MKK6, p38 MAPK, MK2, and/or XBP1. Alternatively, or in addition, compound libraries, or candidate agents from the prior screen, can be screened for compounds that dephosphorylate MKK3, MKK4, MKK6, p38 MAPK, MK2, and/or XBP1. Compound libraries or candidate agents can also be screened for the ability to inhibit MKK3, MKK4, MKK6, p38 MAPK, or MK2 activity and inhibit XBP1 phosphorylation and/or nuclear internalization in vitro or in vivo.

Phosphatase inhibitors identified for use in the disclosed methods are preferably also screened against other map kinase substrates to determine if the compound's activity is specific for phosphatases of MKK3, MKK4, MKK6, p38 MAPK, MK2, and/or XBP1. Compounds that substantially activate or inhibit other enzymes are non-specific and are more likely to case side-effects and toxicity. Candidate phosphatase inhibitors are therefore also preferably tested in vivo for therapeutic effect, side-effects, and toxicity.

C. Pharmaceutical Compositions

Pharmaceutical formulations of the disclosed specific activators of MKK3, MKK4, MKK6, p38MAPK, MK2, and/or XBP1, or other disclosed therapeutic compounds or agents can be used therapeutically in combination with a pharmaceutically acceptable carrier. The disclosed therapeutic compounds can be incorporated in pharmaceutical formulations as neutral compounds, pharmaceutically acceptable salts, and/or prodrugs. Pharmaceutical formulations can be designed for immediate release, sustained release, delayed release and/or burst release of one or more specific activators of MKK3, MKK4, MKK6, p38MAPK, MK2, and/or XBP1 in a therapeutically effective amount. In a preferred embodiment, the formulation provides an initial burst release of a "loading dosage", followed by a sustained release to maintain the therapeutically effective dosage. This can be accomplished using a delayed and/or extended release formulation.

The materials may be in solution, suspension (for example, incorporated into microparticles, liposomes, or cells). Pharmaceutical carriers are known to those skilled in the art. These most typically would be standard carriers for administration of drugs to humans, including solutions such as sterile water, saline, and buffered solutions at physiological pH.

Pharmaceutical compositions may include carriers, thickeners, diluents, buffers, preservatives, and surface active agents.

In some embodiments, the compositions may be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The pharmaceutical compositions can be formulated for any route of administration suitable for targeting liver cells in a subject. In preferred embodiments, the pharmaceutical compositions are formulated for parental or oral administration.

1. Formulations for Parenteral Administration

The compounds described herein can be formulated for parenteral administration. Parenteral formulations can be prepared as aqueous compositions using techniques is known in the art. Typically, such compositions are prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes. The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

The parenteral formulations described herein can be formulated for controlled release including immediate release, delayed release, extended release, pulsatile release, and combinations thereof.

For example, the compounds and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

2. Oral Formulations

Compositions for oral administration include powders or granules, suspensions or solutions in water or non-aqueous media, capsules, sachets, or tablets. Thickeners, flavorings, diluents, emulsifiers, dispersing aids or binders, and surfactants, may be desirable.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pre-gelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pre-gelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Some of the materials which are suitable as binders can also be used as matrix-forming materials such as hydroxypropyl methyl cellulose, ethyl cellulose, and microcrystalline cellulose.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pre-gelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate.

Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl.beta.-iminodipropionate, myristoamphoacetate, lauryl betaine and lauryl sulfobetaine.

If desired, the tablets, beads, granules or particles may also contain minor amount of nontoxic auxiliary substances such as wetting or emulsifying agents, dyes, pH buffering agents, and preservatives.

Delayed release in an oral formulation can be achieved using enteric coatings. The enteric coated formulation remains intact or substantially intact in the stomach but dissolves and releases the contents of the dosage form once it reaches the small intestine. Other types of coatings can be used to provide delayed release following injection subcutaneously, intra-tissue or intramuscularly at a site near or at the area to be treated.

3. Nasal, Pulmonary or Other Mucosal Formulations

The disclosed compositions can be formulated for delivery to the respiratory system or other mucosa. Suitable formulations for administration of pharmaceutical compositions to the respiratory system include nasal and pulmonary formulations. For example, compositions can be delivered to the respiratory system from an inhalation device, including a dry powder inhaler (DPI), metered-dose-inhaler (MDI), nebulizer, or by an instillation technique. Various suitable devices and methods of inhalation which can be used to administer compositions to a patient's respiratory tract are known in the art, including, but are not limited to, the Spinhaler® (Fisons, Loughborough, U.K.), Rotahaler® (Glaxo-Wellcome, Research Triangle Technology Park, N.C.), FlowCaps® (Hovione, Loures, Portugal), Inhalator® (Boehringer-Ingelheim, Germany), the Aerolizer® (Novartis, Switzerland), the diskhaler (Glaxo-Wellcome, RTP, NC).

A formulation for intranasal administration may include solutions, suspensions or emulsions of the active compound in a liquid carrier in the form of drops, mists, sprays, aerosols, or atomizers. Suitable liquid carriers include water, propylene glycol and other pharmaceutically acceptable alcohols. The formulation may be sterilized, as required. The formulation may also contain adjuvants such as preservatives, stabilizers, emulsifiers or suspending agents, wetting agents, salts for varying the osmotic pressure or buffers, as required. The nasal formulations may also be administered in the form of a powder. For example, a powdery nasal composition can be directly used as a powder for a unit dosage form. If desired, the powder can be filled in capsules such as hard gelatine capsules. The contents of the capsule or single dose device may be administered using e.g. an insufflator. Preferably, it is provided with means ensuring dosing of a substantially fixed amount of composition/actuation.

D. Kits

One or more of the compositions described herein can be assembled in kits, together with instructions for use. Kits can include one or more containers containing a pharmaceutical composition including a therapeutically effective amount of a specific activator of MKK3, MKK4, MKK6, p38 MAPK, MK2, and/or XBP1. Such kits can further include, if desired, one or more of various conventional pharmaceutical kit components, such as, for example, containers with one or more pharmaceutically acceptable carriers as will be readily apparent to those skilled in the art. The kit may also include means of administration, such as one or more of a syringe (e.g., a barrel syringe or a bulb syringe), intravenous (IV) bag, IV line, IV needle, and/or cannula. Printed instructions, either as inserts or as labels, indicating quantities of the components to be administered, guidelines for administration, and/or guidelines for mixing the components, can also be included in the kit.

III. Methods

A. Reducing Blood Glucose

The disclosed pharmaceutical compositions can be used to reduce blood glucose levels in a subject with high blood sugar. Normal fasting glucose levels are generally in the range of about less than 110 mg/dL. Shortly after eating, the blood glucose level may rise temporarily up to 140 mg/dL. Fasting blood glucose levels over 126 mg/dL, and plasma glucose 2 hours after eating over 200 mg/dL are indicative of metabolic disorders, such as type-2 diabetes. Therefore, in preferred embodiments, the pharmaceutical compositions are administered in amounts effective to reduce fasting blood glucose levels in the subject to less than 130 mg/dL, preferably less than 110 mg/dL, and/or the plasma glucose 2 hours after eating to less than 200 mg/dL, preferably less than 140 mg/dL.

Efficacy of the disclosed methods can be monitored by measuring changes in blood glucose levels, body weight, $O_2$ consumption, and % and total body fat content. A statistically significant change in any of these parameters can be considered evidence of therapeutic efficacy. It is preferred that a given marker change by at least 5%, at least 10%, at least 20%, at least 30%, at least 50% or more in effective therapy. Dosage of the pharmaceutical compositions can be modified by the physician to increase efficacy while avoiding side effects or toxicity.

B. Administration

The disclosed pharmaceutical compositions may be administered in a number of ways. The compositions are preferably administered parenterally or orally. In some embodiments, the disclosed compositions may be administered transdermally, ophthalmically, vaginally, rectally, pulmonary or intranasally.

Parenteral administration of the composition, if used, is generally characterized by injection. Examples of parental administration include intravenous, intraperitoneal, intramuscular, subcutaneous, and intracavity injection. Injectables can be prepared in conventional forms, either as liquid solutions or suspensions, solid forms suitable for solution of suspension in liquid prior to injection, or as emulsions. Parenteral administration can also involve use of a slow release or sustained release system such that a constant dosage is maintained.

The disclosed pharmaceutical compositions may also be administered prophylactically to subjects. Thus, the disclosed methods can further involve the step of identifying a subject at risk for a disease or disorder prior to administration of the disclosed compositions.

The exact amount of the compositions required will vary from subject to subject, depending on the species, age, weight and general condition of the subject, the severity of the allergic disorder being treated, the particular compound or agent used, and its mode of administration. An appropriate amount can be determined by one of ordinary skill in the art using routine experimentation. For example, effective dosages and schedules for administering the compositions may be determined empirically, and making such determinations is within the skill in the art. The dosage ranges for the administration of the compositions are those large enough to produce a desired effect. The dosage should not be so large as to cause adverse side effects, such as liver toxicity. Generally, the dosage will vary with the age, condition, sex and extent of the disease in the patient, route of administration, or whether other drugs are included in the regimen. The dosage can be adjusted by the individual physician in the event of any counter indications. Unit dosages can vary depending on the frequency of administration. For example, the composition can be administered in one or more dose administrations daily, for one or several days. Guidance can be found in the literature for appropriate dosages for given classes of pharmaceutical products.

In one embodiment, specific activators of MKK3, MKK4, MKK6, p38 MAPK, MK2, and/or XBP1 are administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of specific activators of MKK3, MKK4, MKK6, p38 MAPK, MK2, and/or XBP1 administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The specific activators of MKK3, MKK4, MKK6, p38MAPK, MK2, and/or XBP1 may be administered one or more times a day. The duration of the treatment may be once per day for a period of about 1, 2, 3, 4, 5, 6, 7, 8, 9, 10 days or more. Subsequent dosage units can be administered any time following the initial administration such that a therapeutic effect is achieved.

Area under the curve (AUC) refers to the serum concentration (nmol/L) of specific activators of MKK3, MKK4, MKK6, p38MAPK, MK2, and/or XBP1 over a given time following the IV administration of the reference specific activators of MKK3, MKK4, MKK6, p38MAPK, MK2, and/or XBP1 standard. By "reference specific activators" is intended a formulation of specific activators of MKK3, MKK4, MKK6, p38MAPK, MK2, and/or XBP1 that serves as the basis for determination of the total specific activators of MKK3, MKK4, MKK6, p38MAPK, MK2, and/or XBP1 dose to be administered to a human subject to achieve the desired positive effect, i.e., a positive therapeutic response that is improved with respect to that observed without administration of specific activators of MKK3, MKK4, MKK6, p38MAPK, MK2, and/or XBP1.

In a preferred embodiment, the dose of specific activators of MKK3, MKK4, MKK6, p38MAPK, MK2, and/or XBP1 to be administered provides a final serum level of specific activators of MKK3, MKK4, MKK6, p38MAPK, MK2, and/or XBP1 of about 100 ng/ml to about 1000 ng/ml, about 1100 ng/ml to about 1450 ng/ml, 100 ng/ml to about 250 ng/ml, about 200 ng/ml to about 350 ng/ml, about 300 ng/ml to about 450 ng/ml, about 350 ng/ml to about 450 ng/ml, about 400 ng/ml to about 550 ng/ml, about 500 ng/ml to about 650 ng/ml, about 600 ng/ml to about 750 ng/ml, about 700 ng/ml to about 850 ng/ml, about 800 ng/ml to about 950 ng/ml, about 900 ng/ml to about 1050 ng/ml, about 1000 ng/ml to about 1150 ng/ml, about 100 ng/ml to about 1250 ng/ml, about 1200 ng/ml to about 1350 ng/ml, about 1300 ng/ml to about 1500 ng/m. In specific embodiments, the serum level of specific activators of MKK3, MKK4, MKK6, p38MAPK, MK2, and/or XBP1 is about 100 ng/ml, 250 ng/ml, 300 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 500 ng/ml, 750 ng/ml, 900 mg/ml, 1200 ng/ml, 1400 ng/ml, or 1600 ng/ml.

In some embodiments, the final serum level of specific activators of MKK3, MKK4, MKK6, p38MAPK, MK2, and/or XBP1 is at least an amount effective to detectably increase phosphorylation of MKK3, MKK4, MKK6, p38MAPK, MK2, and/or XBP1 in liver cells of the subject.

C. Screening Methods

Screening systems and methods for identifying an agent that reduces blood glucose in a subject are also provided. In some embodiments, the method involves contacting MKK3, MKK4, MKK6, p38MAPK, MK2, and/or XBP1 proteins (or fragments thereof) with a candidate agent and assaying for an effect, such as binding, phosphorylation, dephosphorylation, and kinase activity. In addition, XBP1 can be assayed for activation, e.g., nuclear localization. In some embodiments, the method involves contacting a sample containing X-box binding protein 1 (XBP1) with a candidate agent and assaying for an effect, such as binding, phosphorylation, dephosphorylation, and kinase activity. In some embodiments, the method involves detecting phosphorylation of XBP1, wherein an increase in XBP1 phosphorylation (e.g., at residues Thr48, Ser61, or a combination thereof) compared to a control identifies a candidate agent for reducing blood glucose in a subject. In other embodiments, the method involves contacting a sample containing XBP1 with a candidate agent and detecting cellular localization of XBP1, wherein an increase in XBP1 nuclear translocation compared to a control identifies an agent for reducing blood glucose in a subject. In still other embodiments, the method involves contacting a sample containing p38MAPK with a candidate agent and detecting phosphorylation of p38MAPK, wherein an increase in p38MAPK phosphorylation (e.g., Thr180, Tyr182, or a combination thereof) compared to a control identifies an agent for reducing blood glucose. In still other embodiments, the method involves contacting a sample containing MK2 with a candidate agent and detecting phosphorylation of MK2, wherein an increase in MK2 phosphorylation (e.g., TT334) compared to a control identifies an agent for reducing blood glucose.

1. Binding

The binding of candidate agents to MKK3, MKK4, MKK6, p38MAPK, MK2, or XBP1 can be detected using routine methods, such as immunodetection methods, that do not disturb protein binding. The methods can be cell-based or cell-free assays. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

2. Phosphorylation

A classical method of directly detecting protein phosphorylation involves the incubation of whole cells with radiolabeled $^{32}$P-orthophosphate, the generation of cellular extracts, separation of proteins by SDS-PAGE, and exposure to film. Other traditional methods include 2-dimensional gel electrophoresis, a technique that assumes phosphorylation will alter the mobility and isoelectric point of the protein. More recently, the development of phosphorlyation state-specific (phospho-specific) antibodies have provided a means to detect phosphorylation of specific amino acid residues. The antibodies are generally produced by immunizing animals with synthetic phosphopeptides representing the amino acid sequence surrounding the phosphorylation site of the target protein. The immune sera is applied to a peptide affinity column to generate a highly specific immunoreagent. These phospho-specific antibodies are then used in immunoassays to detect phosphorylated protein.

3. Kinase Activity

Protein kinases are often common elements in multiple signaling networks influencing numerous downstream effectors responsible for a biological response. Kinase activity within a biological sample is commonly measured in vitro by incubating the immunoprecipitated kinase with an exogenous substrate in the presence of ATP. Measurement of the phosphorylated substrate can be assessed by several reporter systems including colorimetric, radioactive, or fluorometric detection. Although information can be obtained regarding the actions of a specific kinase, assessing enzyme activity in cellular extracts only provides a glimpse of the signaling landscape. Little is revealed about the proteins being modified, and in vitro activity assays do not address the role of potential endogenous phosphatase activity. Direct detection of phosphorylated proteins can provide a more detailed analysis of the cellular response to an external stimulus, as identification of a phosphopeptide provides information regarding the expression and the functional state of that protein.

4. Candidate Agents

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s). Accordingly, virtually any number of chemical extracts or compounds can be screened using the exemplary methods described herein. Examples of such extracts or compounds include, but are not limited to, plant-based, fungal-based, prokaryotic-based, or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-based, lipid-based, peptide-based, polypeptide-based and nucleic acid-based compounds. Synthetic compound libraries and libraries of natural compounds in the form of bacterial, fungal, plant, and animal extracts are commercially available from a number of sources. In addition, natural and synthetically libraries can be produced, if desired, according to routine methods, e.g., by standard extraction and fractionation methods. Furthermore, if desired, any library or compound is readily modified using standard chemical, physical, or biochemical methods.

When a crude extract is found to have a desired activity, further fractionation of the positive lead extract may be necessary to isolate chemical constituents responsible for the observed effect. The goal of the extraction, fractionation, and purification process is the careful characterization and identification of a chemical entity within the crude extract having the desired activity. The disclosed assays can also be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using appropriate in vitro or animal models.

Candidate agents encompass numerous chemical classes, but are most often organic molecules, e.g., small organic compounds having a molecular weight of more than 100 and less than about 2,500 daltons. Candidate agents contain functional groups necessary for structural interaction with proteins, particularly hydrogen bonding, and typically include at least an amine, carbonyl, hydroxyl or carboxyl group, for example, at least two of the functional chemical groups. The candidate agents often contain cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

The present invention will be further understood by reference to the following non-limiting examples.

EXAMPLES

Example 1

SAPK Signaling Upregulates XBP1

Materials and Methods
Cell Culture

MEF cells were from American Type Tissue Collection (ATCC). These cells were grown in Dulbecco's Modified Eagel Medium (DMEM) supplemented with 10% fetal bovine serum (FBS), 10 U/ml penicillin and 1 µg/ml streptomycin at 37° C. and 5% $CO_2$. Fao cells were maintained in RPMI 1640 medium (Invitrogen) supplemented with 10% fetal bovine serum (FBS), 10 U/ml penicillin and 1 µg/ml streptomycin.

Recombinant XBP1s

Recombinant XBP1s was produced at GenScript. XBP1s CDS together with 6×His-TF tag at N-terminal was cloned into pGSC1 plasmid. The sequences of His-TF tag (6×His+TF tag+3C protease cleavage site) are as follow:

```
                                        (SEQ ID NO: 1)
MNHKVHHHHHHMQVSVETTQGLGRRVTITIAADSIETAVKSE

LVNVAKKVRIDGFRKGKVPMNIVAQRYGASVRQDVLGDLMSRNFID

AIIKEKINPAGAPTYVPGEYKLGEDFTYSVEFEVYPEVELQGLEAIEV

EKTIVEVTDADVDGMLDTLRKQQATWKEKDGAVEAEDRVTIDFTGSV

DGEEFEGGKASDFVLAMGQGRMIPGFEDGIKGHKAGEEFTIDVTFPE
```

-continued

EYHHAENLKGKAAKFAINLKKVEERELPELTAEFIKRFGVEDGSVEGL

RAEVRKNMERELKSAIRNRVKSQAIEGLVKANDIDVPAALIDSEIDVL

RRQAAQRFGGNEKQALELPRELFEEQAKRRVVVGLLLGEVIRTNELK

ADEERVKGLIEEMASAYEDPKEVIEFYSKNKELMDNMRNVALEEQA

VEAVLAKAKVTEKETTFNELMN QQASAGLEVL FQGP.

For producing recombinant XBP1s protein, 5 ng pGSC1 plasmid containing XBP1s and His-TF tag was transformed into ArcticExpress™ (DE3) RP host stain E. coli. The total protein was extracted and purified by Ni-affinity resin.

Adenovirus Production and Infection

Adenovirus expressing XBP1s T48A, XBP1s S61A, XBP1s T48A/S61A and MKK6Glu were produced with ViraPower Adenoviral Expression System (Invitrogen) according to manufacturer's instruction. Briefly, pAD-XBP1s T48A, pAD-XBP1s S61A, pAd-XBP1s T48A/S61A and pAd-MKK6Glu were linearized by restriction endonuclease digestion with Pad and transfected to 293A cells by Lipofectamine. The media was changed with fresh media every other day until the cytopathic effect was observed. When cytopathic effect reached to 80%, cells were collected by centrifugation. The pellet was resuspended in PBS and subjected to freezing and thawing cycles at −80° C. and 37° C. for 4 times. The supernatant containing the virus was prepared by centrifugation at 4,000 rpm for 20 min at room temperature. Ad-XBP1s and Ad-Cre were generated as described previously (Ozcan, L., et al. (2009) *Cell metabolism* 9:35-51). For infection, cells were incubated with adenovirus in reduced volume of medium containing 1% FBS and antibiotics. Cells were gently rocked every 15 min for 1 h to increase efficiency of infection, and then fresh medium were added and cells were incubated for additional 15 h or 23 h.

Total Protein Extraction from Cells

Cells were lysed in lysis buffer (25 mM Tris-HCl, pH 7.4; 10 mM NaF; 10 mM $Na_4P_2O_7$; 2 mM $Na_3VO_4$; 1 mM EGTA; 1 mM EDTA; 1% NP-40; 10 µg/ml Leupeptin; 10 µg/ml Aprotinin; 1 mM PMSF and 20 nM Okadaic acid). After 20 min-rotation at 4° C., cell lysates were centrifuged at 13,200 rpm for 20 min at 4° C. Supernatants were collected and protein concentration was quantified by using Protein Assay Kit (Bio-Rad). The concentrations of protein were normalized with lysis buffer to have equivalent amounts of protein and volume. Protein was denatured by boiling at 100° C. for 5 min in Laemmli buffer. The lysates were cooled to room temperature before loading for western blot analysis.

Western Blot Analysis

Western blot analysis was performed as previously described (Ozcan, L., et al. (2009) *Cell metabolism* 9:35-51). Samples from cell lysates or tissue lysates were resolved by SDS-PAGE and then transferred to polyvinylidene fluoride (PVDF) membrane. After 1 h blocking at room temperature using 10% blocking reagent (Roche), membrane was incubated overnight with primary antibody in Tris-buffered saline solution/Tween (TBST) containing 10% blocking reagent at 4° C. After the incubation, membrane was washed three times in TBST and incubated with secondary antibody for 1 h at room temperature. After three-time washing in TBST, membrane was developed using a chemiluminescence assay system (Roche) and exposed to Kodak films. Relative protein levels were quantified by Image J program.

For stripping, membrane was vigorously shaken in stripping buffer (62.5 mM Tris-HCl, pH 6.7; 2% SDS; 100 mM 2-mecaptomethanol) at 50° C. for 20 min. After stripping, membrane was washed three times in TBST.

Statistical Analysis

Data are presented as means±standard error of the mean (SEM). Statistical significance was calculated by Student's t test or by multifactor analysis of variance (ANOVA), with factors of time, treatment, and in some cases, genotype. Non-significant interaction terms involving time were taken as an indication that treatment contrasts could be pooled across time. When ANOVA indicated a significant difference among the groups, the groups were compared using a stricter criterion for statistical significance according to the Bonferroni rule (corrected p value=pair-wise p value x number of groups). Significance was accepted at the level of $p<0.05$ (*), $p<0.01$ (), or $p<0.001$ (*).

Results

XBP1s is a central regulator of ER homeostasis. To investigate whether activation of JNK or p38 MAPK affects XBP1s activity, XBP1s was expressed in MEFs by infecting them with XBP1s-expressing adenovirus (Ad-XBP1s), or with LacZ-expressing adenovirus (Ad-LacZ; control). Subsequently, the cells were treated for two hours with increasing doses of anisomycin, an agent that increases JNK and p38 MAPK activation. Anisomycin treatment led to a robust increase in XBP1s protein levels, but only in cells infected with Ad-XBP1s. No upregulation of XBP1s proteins was noted in Ad-LacZ-infected control cells treated with up to 25 ng/ml anisomycin, showing that anisomycin by itself does not create ER stress nor does it induce XBP1 splicing. A time course experiment demonstrated that exposure of the XBP1s-expressing cells to anisomycin (25 ng/ml) leads to upregulation of XBP1s protein levels within the first 30 minutes. To determine whether an alternative way of activating SAPKs would also increase XBP1s protein levels, XBP1s-expressing cells were treated for a period of two hours with increasing doses of TNFα. As with the anisomycin, TNFα stimulation markedly increased XBP1s protein levels. A study of the time course of this effect revealed that TNFα (10 ng/ml) also upregulates XBP1s levels within 30 minutes. And finally, undertaking the same experiment in Fao cells (a rat hepatoma cell line) revealed that Ad-XBP1s-infected Fao cells also respond to anisomycin or TNFα as do the MEFs, by dramatically upregulating their XBP1s levels.

Example 2

SAPK Signaling Increases XBP1 mRNA Stability Nuclear Translocation

Materials and Methods

Real-Time Quantitative PCR

Total RNA was extracted from cells or animal tissues using Trizol reagent (Invitrogen) and transcribed into cDNA using cDNA synthesis kit (Bio-Rad). The gene expression analysis was performed with iQ5 Multicolor Real-Time PCR Detection System (Bio-Rad) with SYBR Green Supermix (Bio-Rad). The mRNA level was normalized to 18S as a house keeping gene. The primer sequences used were:

```
18S rRNA forward:
                                        (SEQ ID NO: 2)
5'-AGT CCC TGC CCT TTG TAC ACA-3';

18S rRNA reverse:
```

-continued

5'-CGT TCC GAG GGC CTC ACT-3'; (SEQ ID NO: 3)

XBP1s forward:
5'-GGTCTGCTGAGTCCGCAGCAGG-3'; (SEQ ID NO: 4)

XBP1s reverse:
5'-AGGCTTGGTGTATACATGG-3'. (SEQ ID NO: 5)

Cytoplasmic and Nuclear Protein Extraction

Cytoplasmic and nuclear protein fractions were extracted from cells by using nuclear protein extraction kit from Active Motif (Carlsbad, Calif.). Cells were maintained in 10 cm tissue culture dishes for nuclear/cytoplasmic extraction. After removal of the media, cells were washed with ice-cold phosphate buffered saline (PBS) containing phosphatase inhibitors. Subsequently, 3 ml of ice-cold PBS with phosphatase inhibitors was added and then cells were scrapped out of the dish. Collected cells were separated from PBS by centrifugation for 5 minutes at 500 rpm and resuspended with 500 µl of 1× hypotonic buffer. After 15-minute incubation in hypotonic buffer on ice, 25 µl of supplied detergent was added and cells were vortexed 10 seconds. Cells were centrifuged for 30 seconds at 14,000×g and supernatant (cytoplasmic fraction) was saved for further analysis. Remaining pellet, which contains nuclei, were resuspended with 50 µl of provided complete lysis buffer with 1 mM dithiothreitol (DTT), vortexed 10 seconds, and incubated for 30 minutes on ice. After 30-second vortexing and 10-minute centrifugation at 14,000×g, the supernatant was collected and analyzed as nuclear fraction.

For liver tissue, a kit from Thermo Scientific (Rockford, Ill.) was used according to the manufacturer's instruction. Liver tissues were cut into small pieces, washed with PBS, and separated from PBS by centrifugation at 500×g for 5 minutes. Collected tissues were resuspended by company-supplied CER I buffer and homogenized with a Dounce homogenizer. Homogenized tissues were vortexed and incubated on ice for 10 minutes. Following CER II buffer addition, tissues were vortexed for 5 seconds, incubated for 1 minute on ice, vortexed again, and then centrifuged for 5 minutes at maximum speed in a microcentrifuge. The supernatant (cytoplasmic fraction) was saved for later analysis. The pellets were resuspended with supplied NER buffer and undergone a series of multiple vortexing (15 seconds) and incubation on ice (10 minutes) for a total of 40 minutes. After 10-minute centrifugation, the supernatant (nuclear fraction) was collected and analyzed with immunoblotting.

Results

Figure 2A:
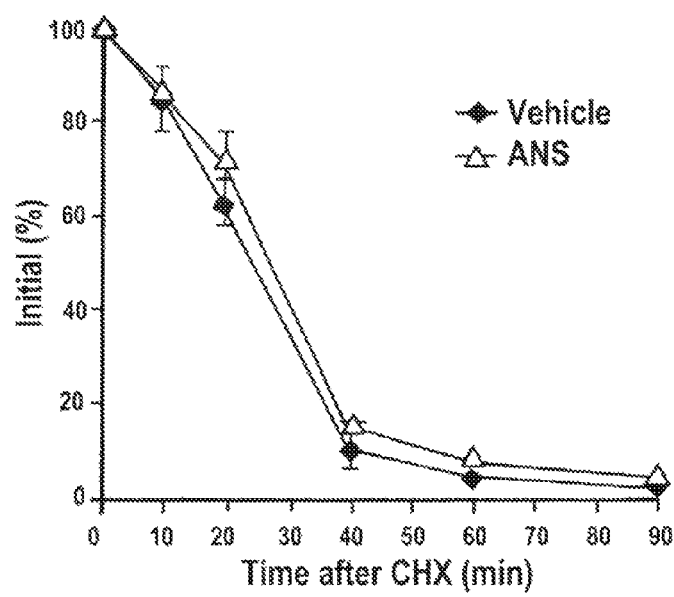
FIG. 2A is a graph showing XBP1s protein/actin ratio (%) in mouse embryonic fibroblasts (MEFs) treated with vehicle (♦) or anisomycin (ANS, ▲) before and at indicated times after addition of cycloheximide (CHX) (10 μg/ml).

To determine whether upregulation of XBP1s levels is due to an increase in the protein stability, cells were infected with Ad-XBP1s, subsequently treated with vehicle or anisomycin (25 ng/ml) for two hours, then further treated with cycloheximide (10 µg/ml) to inhibit the initiation of translation. XBP1s levels were determined before addition of cycloheximide, as well as 10, 20, 40, 60 and 90 minutes after adding it. To analyze the degradation rate of XBP1s in vehicle- and or anisomycin-treated cells correctly, blots from vehicle-treated cells were exposed longer than anisomycin-treated cells to have the same amount of XBP1s signal at 0 time points of both groups. No differences in the degradation rate of XBP1s protein in the vehicle- or anisomycin-treated cells was observed (FIG. 2A). These results exclude the possibility that anisomycin increases XBP1s protein levels by increasing its stability.

Figure 2B:
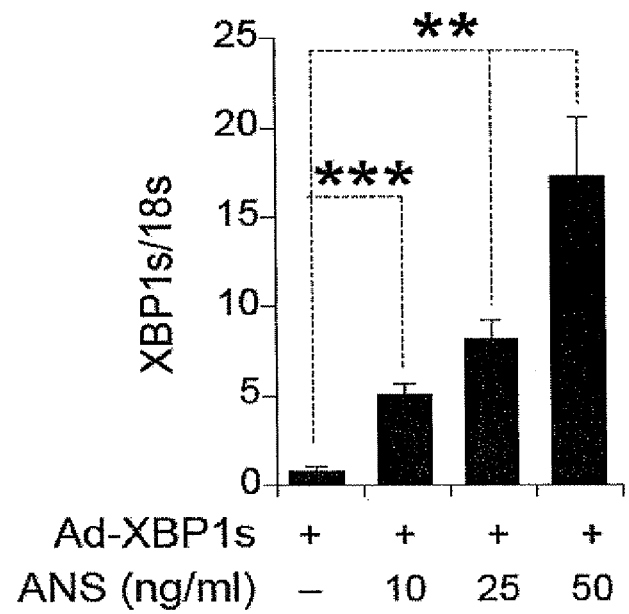
FIG. 2B is a bar graphs showing XBP1s mRNA levels (normalized to 18 S) in MEFs infected with adenoviruses expressing XBP1s (Ad-XBP1s) and subsequently treated with 0, 10, 25, and 50 ng/ml ANS for one hour.
Figure 2C:
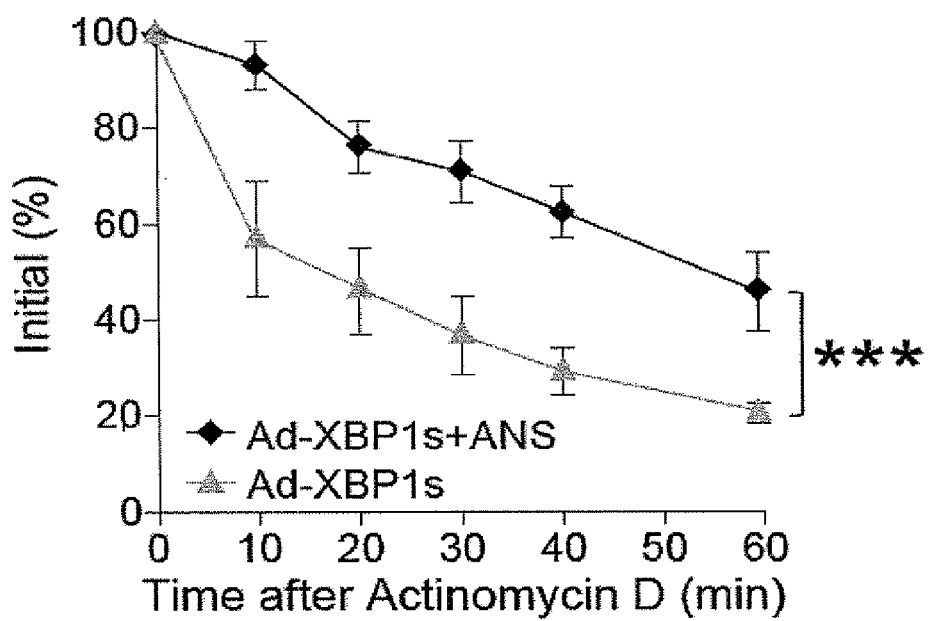
FIG. 2C is a graph showing XBP1s mRNA levels (% change) in MEFs infected with Ad-XBP1s and stimulated with ANS (25 ng/ml) for one hour and then treated with actinomycin D (10 μg/ml) for 0, 10, 20, 30, 40, 50, and 60 minutes.
Figure 2D:
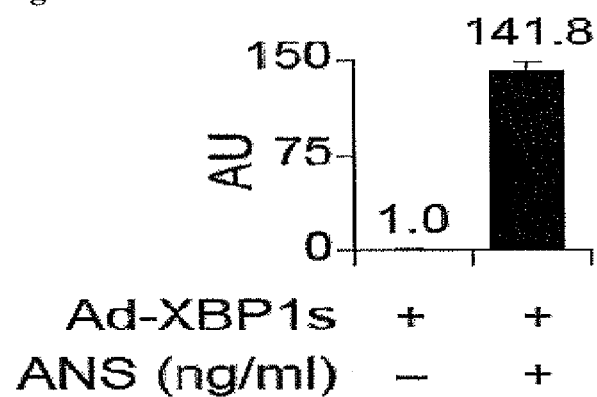
FIGS. 2D and 2E are bar graphs showing nuclear (FIG. 2D) and cytoplasmic (FIG. 2E) XBP1s protein (ratio of ANS-treated versus vehicle-treated cells) in MEFs infected with. Ad-XBP1s following exposure to ANS (25 ng/ml) for two hours. Error bars are ±S.E.M. p<0.01, *p<0.001.
Figure 2E:
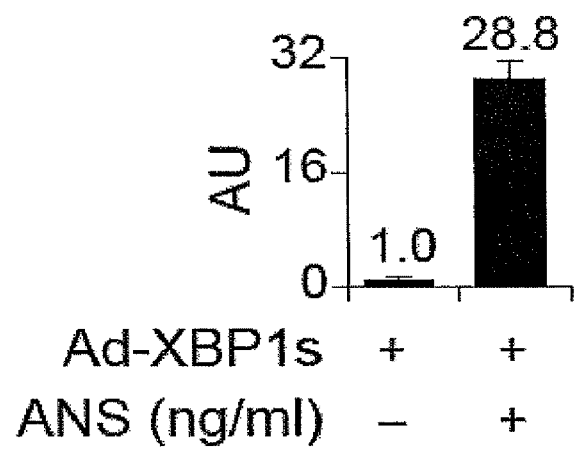

However, upon examining XBP1s mRNA levels in the vehicle-treated and anisomycin-treated XBP1s expressing cells, a dramatic increase in mRNA of XBP1s was noted in the anisomycin-treated cells (FIG. 2B). To evaluate the possibility that anisomycin treatment increases the stability of XBP1s mRNA, the XBP1s expressing cells were pre-treated with anisomycin (25 ng/ml) for one hour, and the degradation pattern of XBP1s mRNA was examined after adding actinomycin D (10 µg/ml—to inhibit transcription). Anisomycin extended the half-life of the mRNA from around 15 minutes to 60 minutes (FIG. 2C). Thus, activation of SAPK signaling increases the half-life of XBP1s mRNA. Furthermore, nuclear levels of XBP1s in anisomycin-treated cells were 141.8 times higher than in vehicle-treated cells, but cytoplasmic levels of the protein were only increased 28.8 times (FIGS. 2D-2E). Under normal conditions, the fold increase in XBP1s should be similar in the cytoplasmic and nuclear compartments. The five-fold discrepancy in these values for the anisomycin-treated cells suggested that anisomycin increases the efficiency of nuclear translocation of XBP1s. When taken together, the results suggested that SAPK signaling increases the mRNA stability of XBP1s and leads to its nuclear translocation with a higher efficiency.

Example 3

XBP1 Upregulation Independent of JNK Activation

Materials and Methods

Plasmids

MKK7-JNK1-expressing plasmids were obtained from Addgene (Cambridge, Mass.).

Results

To unravel the molecular mechanisms underlying the above observations, several different approaches were taken to explore whether activation of JNK, which is one of the most dominant signaling elements in SAPK signaling, affects XBP1s levels and nuclear translocation. First, Ad-LacZ-infected cells and Ad-XBP1s-infected cells were treated with a specific JNK inhibitor (JNK inhibitor VIII, 1.0 µM) for 30 minutes, then exposed to anisomycin (25 ng/ml) for two hours. The JNK inhibitor was effective in completely abolishing anisomycin-induced JNK activation (analyzed via c-Jun phosphorylation), but had no effect on anisomycin-mediated upregulation of XBP1s protein levels. As the second approach, JNK1/2$^{-/-}$ were stimulated with anisomycin, which also led to a significant increase in XBP1s protein that was significantly higher than that in anisomycin-treated control cells. And, while no JNK activity was detectable in the JNK1,2$^{-/-}$ cells that were treated with anisomycin, a marked increase in p38 MAPK phosphorylation was noted. It is known that MAPK kinase kinase (MKK) 4 and 7 are upstream kinases responsible for JNK activation (Tournier, C., et al. (2001) *Genes Dev* 15:1419-1426; Brancho, D., et al. (2003) *Genes Dev* 17:1969-1978) and anisomycin or TNFα cannot activate JNK in MKK4 and 7 double knock out cells (MKK4,7$^{-/-}$) (Tournier, C., et al. (2001) *Genes Dev* 15:1419-1426; Schaeffer, H. J. & Weber, M. J. (1999) *Mol Cell Biol* 19:2435-2444). In order to determine whether XBP1s can be regulated by anisomycin treatment in MKK4, 7$^{-/-}$ cells, these cells, along with their controls, were treated with anisomycin after XBP1s expression. As for the JNK1, 2$^{-/-}$ cells, anisomycin stimulation dramatically increased XBP1s levels in MKK4,7$^{-/-}$ cells, to a level that was significantly higher than that in wt control cells. JNK activity was not detectable in the MKK4,7$^{-/-}$ cells, whereas p38 MAPK activation was significantly increased. Furthermore, the experiments were repeated in JNK1,2$^{-/-}$ and MKK4,7$^{-/-}$ cells with TNFα. As with anisomycin, treatment of JNK1,2$^{-/-}$ and MKK4,7$^{-/-}$ cells with TNFα also led to a significant increase in XBP1s levels. Finally, an MKK7-JNK1 fusion protein, previously shown to be a specific activator of JNK (Lei, K., et al. (2002) *Mol Cell Biol* 22:4929-4942), was used to investigate whether activation of JNK alone can have effect on XBP1s. MKK7-JNK1 expression in the cells significantly increased JNK activation. However, co-expression of MKK7-JNK1 with XBP1s did not increase protein levels of XBP1s, indicating that the process is independent of JNK activation.

Example 4

XBP1 Upregulation Mediated by p38 MAPK

Materials and Methods
Plasmids
MKK6Glu-expressing plasmids were obtained from Addgene (Cambridge, Mass.). For producing adenovirus expressing MKK6Glu, MKK6Glu in pcDNA3.1 was subcloned into pENTR3C (Invitrogen) at the sites of Not I and Kpn I. Primer sequences are: 5'-TTAAG GGTACCGGCGC-CATGTCTCAGTCGA AAGGCAA-3' (forward, SEQ ID NO:6); 5'-TTAAG GCGGCCGCTTATCATTAGTCTC-CAA GAATCAG-3' (reverse, SEQ ID NO:7). The resulting MKK6Glu in pENTR3C was further subcloned into pAD (Invitrogen) by using LR clonase (Invitrogen) for generating adenovirus.

Results
p38 MAPK is another critical SAPK signaling element that is activated during ER stress conditions, and in the absence of JNK activation, higher levels of p38 MAPK activation were noted. The possibility that p38 MAPK activation mediates the effects of anisomycin and TNFα on XBP1s was therefore examined. Ad-XBP1s-infected cells were treated with a specific p38 MAPK inhibitor (SB203580) (10 μM for 30 minutes), then stimulated with anisomycin (25 ng/ml) for two hours. The dramatic increase in the XBP1s levels was completely abolished by pretreatment of the cells with a p38 MAPK inhibitor. These findings suggest that anisomycin-induced upregulation of XBP1s levels is mediated via the p38 MAPK pathway.

MKK3 and 6 are required for p38 MAPK activation, and in fact, p38 MAPK cannot be activated in MKK3,6$^{-/-}$ cells (Brancho, D., et al. (2003) *Genes Dev* 17:1969-1978). In light of this, it was reasoned that anisomycin should not induce an increase in XBP1s levels in MKK3,6$^{-/-}$ cells—and indeed, no increase in XBP1s levels was noted when Ad-XBP1s-infected MKK3,6$^{-/-}$ cells were treated with anisomycin, relative to levels in anisomycin-stimulated Ad-LacZ-infected control cells. And, as previously reported (Brancho, D., et al. (2003) *Genes Dev* 17:1969-1978), p38 MAPK activation was dramatically reduced in MKK3,6$^{-/-}$ cells. Ad-XBP1s-infected p38α$^{-/-}$ cells also lacked the ability to upregulate XBP1s levels in response to anisomycin stimulation.

A constitutively active form of MKK6 (MKK6Glu), one of the upstream kinases of p38 MAPK, was previously generated by mutation of Ser207 and Ser211 to glutamate. Expression of MKK6Glu specifically activates p38 MAPK (Raingeaud, J., et al. (1996) *Mol Cell Biol* 16:1247-1255). MKK6Glu was used to assess whether activation of p38 MAPK alone is sufficient to increase XBP1s protein levels. Cells were first transfected with MKK6Glu and/or XBP1s at the presence or absence of p38 MAPK inhibitor (10 μM). Expression of MKK6Glu significantly increased XBP1s protein levels, similar to findings with anisomycin and TNFα. However, inhibition of p38 MAPK activity blocked the effect of MKK6Glu on XBP1s.

Example 5 p38 MAPK Regulates XBP1s mRNA Stability

Materials and Methods
Protein Degradation and mRNA Stability Analysis
MEF cells were infected with Ad-XBP1s. After 24 h post-infection, cells were treated with anisomycin at 25 ng/ml or vehicle (DMSO) for 2 h. Translation initiation inhibitor cycloheximide (10 μg/ml, Sigma) was added to the medium. Cells were flash frozen in liquid nitrogen at various time points. Protein levels were determined via immunoblotting.

For mRNA stability determination, MEF cells were infected with Ad-XBP1s. Sixteen hour after the infection, cells were treated with anisomycin (25 ng/ml) or vehicle (DMSO) for 1 h. Actinomycin D (10 μg/ml, Sigma) was added to the medium. Cells were flash frozen in liquid nitrogen at various time points. mRNA levels were determined via Q-PCR.

Figure 3A:
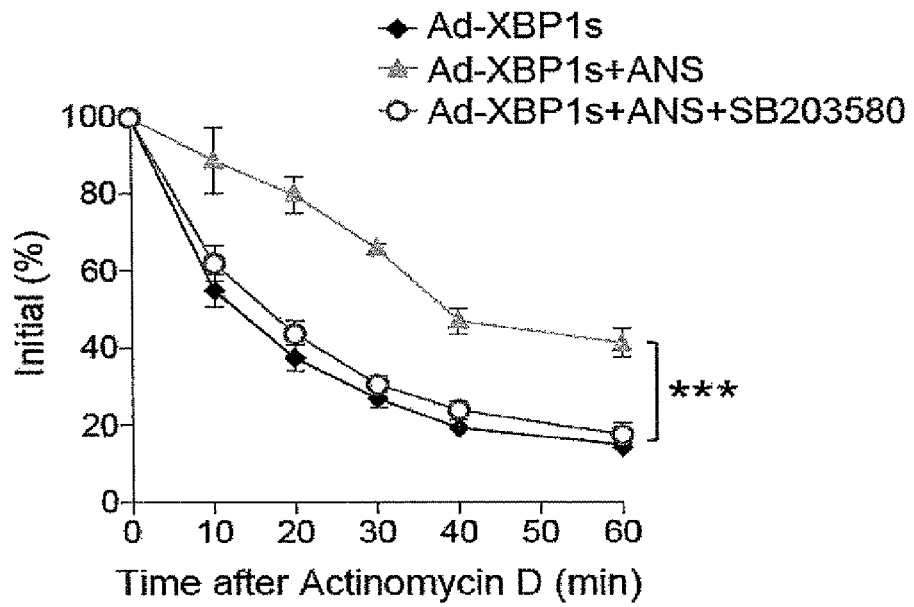
FIG. 3A is a graph showing XBP1s mRNA levels (% change) in MEFs infected with Ad-XBP1s (♦▲●), pretreated with SB203580 (10 μM) for 30 min (●), stimulated with ANS (25 ng/nal) for an additional one hour (▲●) and then treated with actinomycin D (10 μg/ml) for 0, 10, 20, 30, 40, 50, and 60 minutes.

Results
To investigate whether the increased stability of XBP1s mRNA was indeed mediated via the p38 MAPK pathway, cells were pretreated first with a p38 MAPK inhibitor (10 μM) for 30 minutes, then treated with anisomycin (25 ng/ml) for one hour, and finally incubated with actinomycin D (10 μg/ml) to inhibit mRNA transcription. mRNA abundance of XBP1s was analyzed at indicated time points (FIG. 3A). Inhibition of p38 MAPK completely blocked the prolongation of the half-life of XBP1s mRNA induced by anisomycin stimulation (FIG. 3A).

p38 MAPK signaling has also been implicated in the regulation of stability of several different mRNAs (Clark, A., et al. (2009) *Front Biosci* 14:847-871). One of the main molecules that links p38 MAPK activation to regulation of mRNA stability is MAPK-activated protein kinase 2 (MK2) (Clark, A., et al. (2009) *Front Biosci* 14:847-871). MK2 was previously shown to regulate activation of several RNA-binding proteins that are involved in stabilization of mRNA. These include tristetraprolin (TTP), human antigen R (HuR: SLAV family RNA binding protein) or ARE/poly(U)-binding degradation factor (AUF1). In addition p38 MAPK can also regulate RNA stability by directly phosphorylating KH-domain splicing regulatory protein (KSRP) (Clark, A., et al. (2009) *Front Biosci* 14:847-871).

Figure 3B:
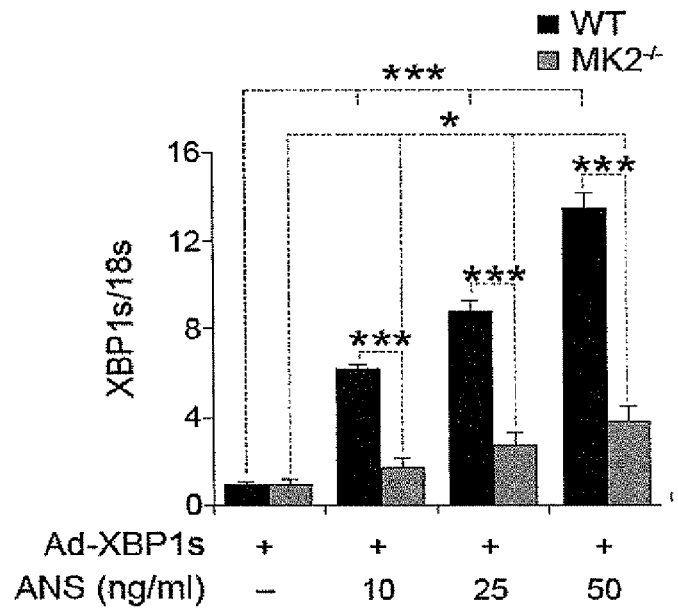
FIG. 3B is a bar graph showing XBP1s mRNA levels (normalized to 18S) in WT (solid bars) and MK2$^{-/-}$ (shaded bars) MEFs infected with Ad-XBP1s and treated with ANS at 0, 10, 25, and 50 ng/ml for one hour.
Figure 3C:
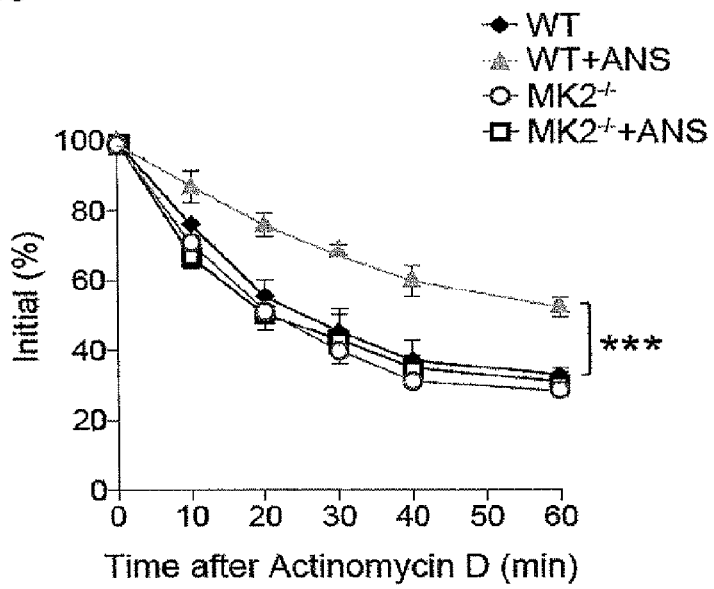
FIG. 3C is a graphs showing XBP1s mRNA levels (% change) in Ad-XBP1s-infected WT (♦▲) and MK2$^{-/-}$ (●■) MEFs stimulated either with vehicle (♦●) or ANS (25 ng/ml) (▲■) and then treated with actinomycin D (10 μg/ml) for 0, 10, 20, 30, 40, 50, and 60 minutes. Error bars are ±S.E.M. *p<0.05, ***p<0.001.

To investigate that the p38 MAPK-mediated increase in mRNA stability of XBP1s is due to MK2 activation, Ad-XBP1s-infected control and MK2$^{-/-}$ cells were stimulated with anisomycin. XBP1s protein levels were dramatically reduced in MK2$^{-/-}$ cells, indicating that increased mRNA stability is primarily mediated via MK2 activation. The mRNA levels of XBP1s were next examined in control and MK2$^{-/-}$ cells that were infected with Ad-XBP1s and stimulated with anisomycin for one hour. Anisomycin increased the mRNA levels of XBP1s in a dose dependent manner in control cells (FIG. 3B), but the increase was significantly lower in the MK2$^{-/-}$ cells (FIG. 3B), supporting a dominant role for MK2 in p38 MAPK-mediated upregulation of XBP1s mRNA stability. Furthermore, an analysis of degradation rate of XBP1s mRNA in control and MK2$^{-/-}$ cells that were either treated with vehicle or anisomycin (25 ng/ml) documented that the enhanced stability of XBP1s mRNA after anisomycin treatment is completely lost in MK2$^{-/-}$ cells (FIG. 3C). There were no differences in the degradation rate of XBP1s mRNA between vehicle-treated control and MK2$^{-/-}$ and anisomycin-treated MK2$^{-/-}$ cells (FIG. 3C). Nevertheless, a significant, but much smaller, upregulation of XBP1s mRNA levels was noted in the MK2$^{-/-}$ cells that were treated with anisomycin (FIG. 3B) This small increase may be due to an increase in transcription of endogenous XBP1s. In fact, XBP1s may have positive impact on its own transcription.

Example 6

AUF1 and KSRP RNA-Binding Proteins not Involved in XBP1s mRNA Stability

Materials and Methods
Gene Silencing Experiments with Lentiviral shRNAs
shRNAs in pLKO vector targeting AUF1 and KSRP were from Sigma-Aldrich. The target sequences for AUF1 are:

```
                                  (shRNA #1, SEQ ID NO: 8)
TGAATGGAAGTATGACGTT;

(shRNA #2, SEQ ID NO: 9)
AGTGGTTATGGGAAAGTAT;

(snRNA #3, SEQ ID NO: 10)
GAGAGTGTAGATAAGGTCA;

(shRNA #4, SEQ ID NO: 11)
CAATGTTGGTCTTAGTAAA.
```

The target sequences for KSRP are: CTGAGAAGATTGCTCACAT (shRNA #1, SEQ ID NO:12); TTGGGAAGAGTATTACAAA (shRNA #2, SEQ ID NO:13); AGCAGATTGACCATGCAAA (shRNA #3, SEQ ID NO:14); GCATCCAGTTCAAGCAAGAT (shRNA #4, SEQ ID NO:15). For generating lentiviral particles, pLP1, pLP2, VSVG and either pLKO empty vector or pLKO-containing AUF1 or KSPR shRNA insert were transfected into 293T packaging cells by using Lipofectamine (Invitrogen). The medium was changed 24 h post-transfection and the viral supernatants were collected three days post-transfection, aliquoted and stored at −80° C. For enhancing infection efficiency of lentivirus, MEF cells were pretreated with polybrene (8 μg/ml, Sigma-Aldrich) overnight, and then cells were infected with lentivirus and medium was changed 24 h after the infections. After 48 h post-infection, puromycin (2 μg/ml, Sigma-Aldrich) was added for selecting stably-infected cells and only puromycin-resistant cells were used in experiments. Cells infected with the lentivirus containing empty vector pLKO used as controls.

Figure 9A:
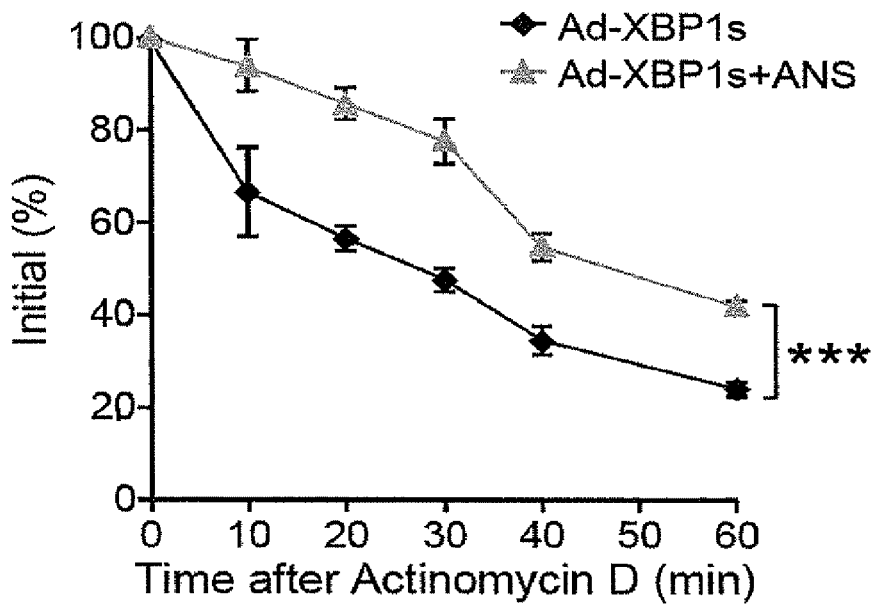
FIG. 9A is a graph showing mRNA levels (% change) of XBP1s in tristetraprolin (TTP) knockout (TTP$^{-/-}$) cells infected with Ad-XBP1s (♦▲) and subsequently treated with ANS (25 ng/ml) (▲) for one hour followed by incubation with actinomycin D (10 μg/ml) for 0, 10, 20, 30, 40, 50, and 60 minutes.

Results
Tristetraprolin (TTP) is a member of a small family of RNA-binding proteins that recognize AU-rich elements (AREs), and is one of the best-known RNA-binding proteins that is the target of MK2. It has been implicated in regulating the stability of a variety of mRNAs (Clark, A., et al. (2009) *Front Biosci* 14:847-871). No classical AREs were identified in the mRNA of XBP1s. In order to determine whether TTP might have a role in stabilizing XBP1s mRNA, Ad-XBP1s-infected TTP$^{-/-}$ cells were treated with anisomycin (25 ng/ml) for one hour, then analyzed for mRNA degradation after inhibition of transcription with actinomycin D (10 μg/ml). Results show that anisomycin is capable of increasing XBP1s mRNA stability even in TTP$^{-/-}$ cells (FIG. 9A):

stimulation with anisomycin led to the same levels of upregulation in XBP1s protein in both wt control and TTP$^{-/-}$ cells.

Figure 9B:
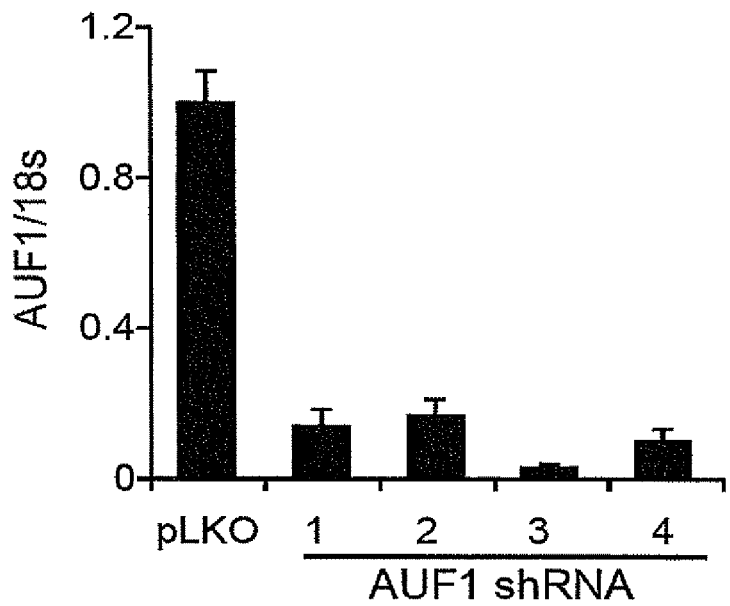
FIGS. 9B and 9C are bar graphs showing mRNA levels (normalized to 18S) of AUF1 (FIG. 9B) and KSRP (FIG. 9C) in cells treated with control pLKO lentiviral vector (FIG. 9B-9C, first bar), lentiviral AUF1 shRNA (FIG. 9B, bars 2-5), or lentiviral KSRP shRNA (FIG. 9B, bars 2-5). Error bars are ±S.E.M. ***p<0.001.

To investigate the role of AUF1 in stabilizing XBP1s mRNA, four lentiviral shRNAs were obtained for AUF1 and MEFs were individually transduced with one of four AUF1 lentiviral shRNAs. shRNA #3 was the most efficient in suppressing AUF1 expression (by more than 90%) (FIG. 9B). After establishing stable AUF1 knock down and control cell lines (pLKO), the cells were infected with Ad-XBP1s and subsequently stimulated with anisomycin. Depletion of AUF1 does not affect anisomycin-induced upregulation of XBP1s levels, indicating that AUF1 is not the RNA binding protein that is involved in stabilization of XBP1s mRNA.

Figure 9C:
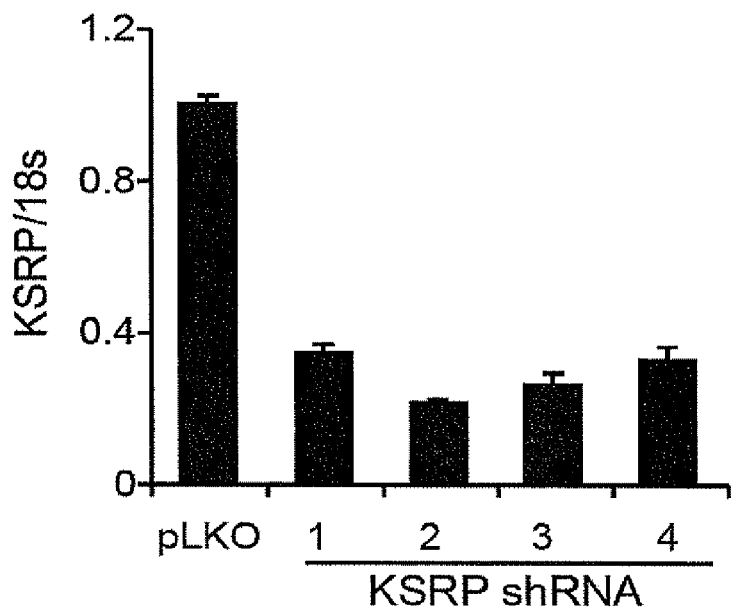

The role of KSRP in regulating stability of XBP1s mRNA was next investigated using the same approach as above for AUF1. shRNAs for KSRP were used it to establish a stable KSRP knock-down cell line, as well as a control (pLKO) cell line (FIG. 9C). Stimulation of KSRP-knocked down cells with anisomycin for two hours revealed that upregulation of XBP1s protein levels was similar between the pLKO controls and KSRP-knocked down cells. Thus, KSRP also does not play a role in XBP1s mRNA stability. And finally, the role of HuR in this process was investigated, but HuR was not detected in MEF cells.

Example 7 p38 MAPK Phosphorylation of XBP1s at Thr48 and Ser61 Critical for Nuclear Translocation of XBP1s Materials and Methods
Mass Spectrometric Analysis by LC-MS/MS
MEFs were infected with flag-tagged XBP1s expressing adenovirus and treated with anisomycin (25 ng/ml) for 2 h. Cells were washed with ice-cold PBS and lysed with RIPA buffer (50 mM Tris-HCl, pH 7.5; 2 mM EGTA; 0.3% CHAPS; 100 mM NaF; 10 mM Na$_4$P$_2$O$_7$; 1 mM Na$_3$VO$_4$; 10 μg/ml Leupeptin; 10 μg/ml Aprotinin; 2 mM PMSF and 20 nM Okadaic acid). After overnight incubation with anti-flag antibody, Protein A sepharose beads were added for additional 2 h at 4° C. Immunoprecipates were washed three times with RIPA buffer containing 150 mM NaCl and boiled for 5 min in 2× Laemmli buffer for elution of immunoprecipitated XBP1s. Samples were resolved in SDS-PAGE and stained with Coomassie blue (Bio-Rad). Protein from Coomassie-stained gel bands was digested with trypsin and the resulting peptide mixtures were subjected to microcapillary liquid chomatography tandem mass spectrometry (LC-MS/MS). MS/MS spectra were assigned by searching them with the XBP1s protein sequence using the SEQUEST algorithm.

Plasmids
Plasmids for amino acid substitution mutants for XBP1s (T48A, S61A and T48A/S61A) were generated by PCR-based mutagenesis using pcDNA3.1-XBP1s or pENTR-XBP1s as template with a kit from Stratagene (La Jolla, Calif.).

```
Primer sequences for T48A are:
                                  (forward, SEQ ID NO: 16)
5'-GGGTCGGAGGCGAGCGGGGCACCGCAGGCTCGCAAGCGG-3';

(reverse, SEQ ID NO: 17)
5'-CCGCTTGCGAGCCTGCGGTGCCCCGCTCGCCTCCGACCC-3'.
```

```
                                    -continued
Primer sequences for S61A are:
                                    (forward, SEQ ID NO: 18)
5'-CAGCGGCTCACGCACCTGGCCCCGGAGGAGAAAGCGC-3';

(reverse, SEQ ID NO: 19)
5'-GCGCTTTCTCCTCCGGGGCCA GGTGCGTGAGCCGCTG-3'.
```

Mutations at specific positions were confirmed by sequencing. The resulting mutated XBP1s in pcDNA3.1 (Invitrogen) were used for transient transfection assays and mutated XBP1 s in pENTR3C were further subcloned into pAD for producing adenovirus.

In Vitro Kinase Assay

5 μg of recombinant XBP1s was incubated with activated recombinant p38α MAPK (Cell Signaling) in kinase assay buffer (25 mM Tris-HCl, pH 7.5; 5 mM β-glycerophosphate; 2 mM dithiothreitol; 0.1 mM $Na_3VO_4$, 10 mM $MgCl_2$) containing 5 μCi of [γ-$^{32}$P]ATP (PerkinElmer) and 10 μM cold-ATP for 30 min at 30° C. in the presence or absence of 10 μM SB203580 (Calbioehem). GST-ATF2 fusion protein (Cell Signaling) was used as a positive control. The reactions were terminated by addition of Laemmli buffer and samples were separated by SDS-PAGE and transferred to PVDF membranes. Total protein levels were detected by immunoblotting and incorporated $^{32}$P (phosphorylation) was visualized by autoradiography.

Results

Figure 4:
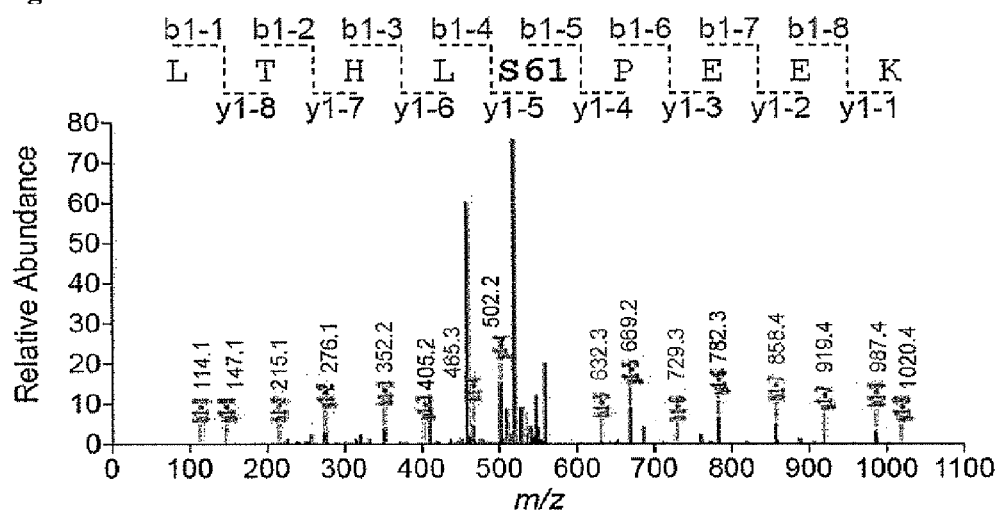
FIG. 4 is a tandem mass spectrometry (MS/MS) graph showing phosphorylation of XBP1s at Ser61 after anisomycin stimulation. The graph plots relative abundance of XBP1 fragments as a function of mass-to-charge ratios (m/z).

The dramatic increase in the efficiency of migration of XBP1s to the nucleus when p38 MAPK is activated was unexpected, and suggested that p38 MAPK directly phosphorylates XBP1s and triggers this enhanced translocation. A flag-tagged-XBP1s was therefore expressed in cells, which were stimulated with anisomycin (25 ng/ml) for two hours. This was followed by immunoprecipitation of XBP1s, resolving with SDS-PAGE, and visualizing with Coomassie blue staining. MS/MS analysis (used to determine the phosphorylation sites on XBP1s) demonstrated that anisomycin stimulation increases phosphorylation of XBP1s at Ser61, which is a conserved phosphorylation site (LSPE) for p38 MAPK (FIG. 4). One other phosphorylation site (Thr48) on XBP1s is also a conserved p38 MAPK phosphorylation site, although it was not detected with the MS/MS analysis.

To convincingly demonstrate that Ser61 is indeed phosphorylated after anisomycin stimulation or via activation of p38 MAPK, and also to test whether Thr48 is also a phosphorylation site, a phospho-specific antibody was developed against phosphorylated XBP1s on Ser61 or on Thr48. Stimulation of XBP1s-expressing cells with anisomycin (25 ng/ml) greatly increased phosphorylation of the Thr48 residue. To unravel the role of this phosphorylation site the Thr48 residue was mutated to alanine (T48A), which completely eliminated the anisomycin-induced phosphorylation of XBP1s$^{Thr48}$ but did not affect the upregulation in XBP1s protein levels. These results also demonstrate that the phospho-specific XBP1s$^{Thr48}$ antibody does not recognize the unphosphorylated XBP1s. Despite the fact that XBP1s and mutant XBP1s-T48A are upregulated to similar levels after anisomycin stimulation, phosphorylation is only recognized in the wt XBP1s. Similar results were obtained from XBP1s$^{Ser61}$ phosphorylation. Anisomycin stimulation strongly induced phosphorylation of XBP1s at Ser61, but mutation of Ser61 did not alter the anisomycin-induced upregulation of XBP1s protein levels. As with the p-XBP1s$^{Thr48}$ antibody, these results also establish the fact that the p-XBP1$^{Ser61}$ antibody is specific for XBP1s that is phosphorylated on Ser61.

To determine whether p38 MAPK can directly phosphorylate XBP1s, and whether anisomycin-induced phosphorylation of XBP1s at Thr48 and Ser61 is directly mediated via p38 MAPK, a His/TF-tagged-XBP1s was first cloned into a pGS21a bacterial expression vector, and the XBP1s fusion protein purified in a *E. coli* strain-(ArcticExpress™ (DE3) RP host strain). Following successful purification of the XBP1s protein, an in vitro kinase assay was performed with an already activated recombinant p38 MAPK protein. Incubation of XBP1s with activated recombinant p38 MAPK significantly increased phosphorylation of XBP1s, however, addition of a p38 MAPK inhibitor to the kinase assay buffer completely reversed the effect of activated p38 MAPK on XBP1s. As a control, the p38 MAPK kinase assay was also done with ATF2. Results demonstrated that activated recombinant p38 MAPK is fully functional and phosphorylates ATF2, and that this phosphorylation is inhibited by p38 MAPK inhibitor. In addition, an in vitro kinase assay was aimed at understanding whether Thr48 and Ser61 are indeed directly phosphorylated by p38 MAPK. Direct immunoblotting with use of the phospho-specific antibodies for p-XBP1s$^{Thr48}$ and p-XBP1s$^{Ser61}$ demonstrated that p38 MAPK directly phosphorylates XBP1s on Thr48 and Ser61 residues in the in vitro kinase assay. To understand the role of these phosphorylations, and to exclude a possible overlapping function in regulation of XBP1s activity and nuclear translocation, a double mutant XBP1s was created at Thr48/Ser61 residues.

The contribution of each phosphorylation site was then investigated on the nuclear translocation of XBP1s. WT, T48A, S61A and T48A/S61A mutant XBP1s were expressed in the cells, anisomycin (25 ng/ml) was added, and total levels of cytoplasmic and nuclear XBP1s proteins were determined. Mutation of Thr48, of Ser61, or of both sites together, did not affect the anisomycin-stimulated upregulation of XBP1s protein levels. However, mutation of the Thr48 residue decreased XBP1s nuclear translocation by about 49%, mutation of the Ser61 residue decreased it by about 79%, while mutation of both sites almost completely blocked nuclear translocation of XBP1s. In the mean time, mutation of Thr48 and Ser61 led to accumulation of XBP1s in the cytoplasm indicating that the double mutant XBP1s, despite the dramatic increase in the protein levels can not migrate to the nucleus. These findings indicate that Thr48 and Ser61 phosphorylation is crucial for nuclear translocation of XBP1s.

Example 8 p38 MAPK Activation and Signaling Necessary for XBP1s Nuclear Translocation

Materials and Methods

Total Protein Extraction from Tissue

Tissues were homogenized with a bench-top homogenizer (Polytron, PT2100) in ice-cold tissue lysis buffer (25 mM Tris-HCl, pH 7.4; 100 mM NaF; 50 mM $Na_4P_2O_7$; 10 mM $Na_3VO_4$; 10 mM EGTA; 10 mM EDTA; 1% NP-40; 10 μg/ml Leupeptin; 10 μg/ml Aprotinin; 2 mM PMSF and 20 nM Okadaic acid). After homogenization, lysates were rotated for 1 h at 4° C. and then subjected to centrifugation at 13,200 rpm for 20 min at 4° C. The lipid layer was removed and the supernatant was transferred into Eppendorf tubes for centrifugation. This process was repeated for 2 times to get rid of lipid completely. Protein concentration was quantified by using Protein Assay Kit (Bio-Rad). Equivalent protein concentration in each sample was prepared and boiled at 100° C. for 5 min in Laemmli buffer. The lysates were cooled to room temperature before loading for western blot analysis.

XBP1 Splicing Assay

XBP1 splicing assay was performed by PCR with cDNA as template. The PCR conditions were as follows: 94° C. for 3 min; 29 cycles of 94° C. for 30 sec, 58° C. for 30 sec, and 72° C. for 30 sec; and 72° C. for 3 min. The primer sequences are:

```
Forward:
                                   (SEQ ID NO: 20)
5'-ACACGCTTGGGAATGGACAC-3';

Reverse:
                                   (SEQ ID NO: 21)
5'-CCATGGGAAGATGTTCTGGG-3'.
```

Results

Figure 10A:
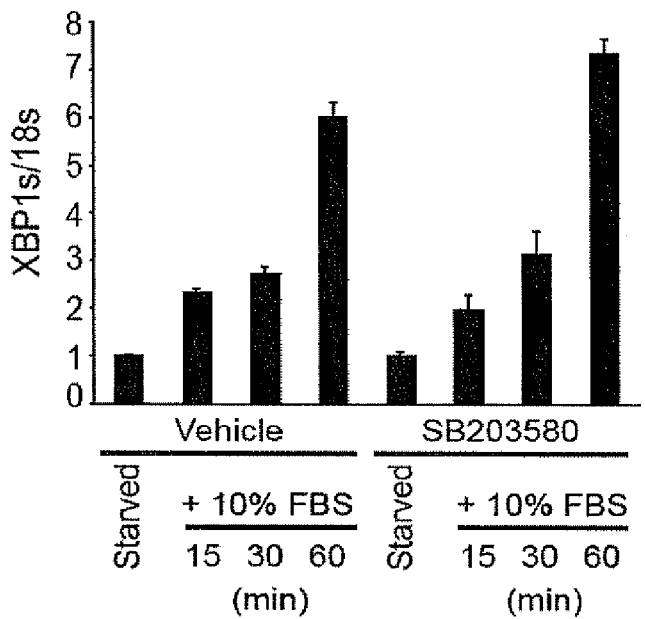
FIG. 10A is a bar graph showing XBP1s mRNA levels (normalized to 18S) in MEFs starved 16 hours in serum-free medium in the absence (bars 1-4) or presence (bars 5-8) of p38 MAPK inhibitor SB203580 (10 μM) and reincubated in medium containing 10% FBS for 0 (bars 1 and 5), 15 (bars 2 and 6), 30 (bars 3 and 7) and 60 (bars 4 and 8) minutes.
Figure 10B:
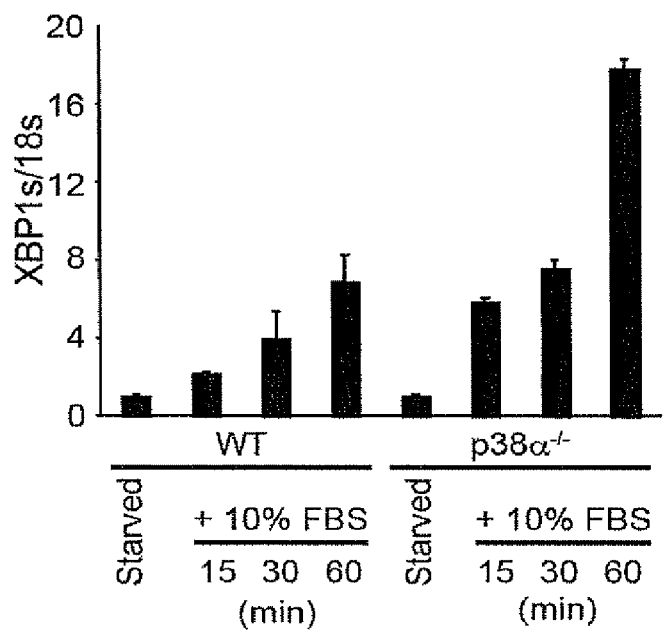
FIGS. 10B and 10C are bar graphs showing XBP1s mRNA levels (normalized to 18S) in wild-type (WT) (FIGS. 10B and 10C, bars 1-4) and p38α$^{-/-}$ (FIG. 10B, bars 5-8), and MKK3,6$^{-/-}$ (FIG. 10C, bars 5-8) cells starved 16 hours in serum-free medium and reincubated in medium containing 10% FBS for 0 (bars 1 and 5), 15 (bars 2 and 6), 30 (bars 3 and 7) and 60 (bars 4 and 8) minutes.
Figure 10C:
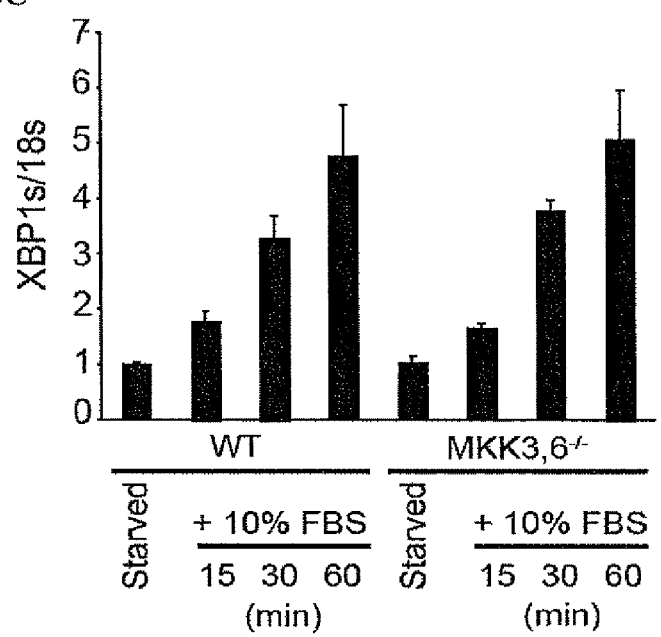

XBP1s is generated in the liver when an animal is refed after a fasting period (Park, S. W., et al. (2010) *Nature Med* 16:429-437), likely mainly due to increased metabolic overloading. To create a metabolic overloading model in cells, following a 16 h starvation in medium without fetal bovine serum (FBS), cells were reineubated for 15, 30 and 60 minutes with medium containing 10% FBS, following which total and nuclear proteins or mRNA were isolated and used to analyze various parameters, including p38 MAPK activation, XBP1s nuclear migration, and splicing. When the cells were starved, then stimulated with medium containing 10% FBS, there was a robust increase in XBP1s splicing and nuclear translocation, as well as in activation of p38 MAPK (FIG. 10A). However, inhibition of p38 MAPK activity by pretreatment of the starved cells with p38 MAPK inhibitor (10 µM) before addition of 10% FBS completely eliminated XBP1s nuclear translocation without altering XBP1s splicing, or without affecting the total amount of XBP1s that is produced in the cells (FIG. 10A). The same experiment was then repeated in p38α$^{-/-}$ and MKK3,6$^{-/-}$ cells. FBS-induced XBP1s nuclear translocation was dramatically reduced in p38α$^{-/-}$ cells compared to control cells, despite the fact that XBP1s splicing and protein levels were similar in control and p38α$^{-/-}$ cells (FIG. 10B). Moreover, FBS-induced XBP1s nuclear translocation was severely impaired in the MKK3,6$^{-/-}$ cells (FIG. 10C). Together, these results indicate that activation of p38 MAPK is necessary for XBP1s nuclear translocation.

To determine whether re-feeding after a fasting period induces p38 MAPK activation and XBP1s phosphorylation in the, wild-type (wt) lean mice were fasted for 24 hours and re-fed for one hour. p38 MAPK phosphorylation was significantly increased in the liver following refeeding, and XBP1s total proteins were upregulated. Also, phosphorylation of XBP1s at Thr48 and Ser61 was markedly increased after re-feeding, indicating that XBP1s is phosphorylated at these sites during the re-feeding process and that refeeding leads to a robust upregulation in nuclear levels of XBP1s.

XBP1s cannot migrate to the nucleus in the liver of obese mice during refeeding (Park, S. W., et al. (2010) *Nature Med* 16:429-437). Consistently, re-feeding ob/ob mice after the fasting period does not increase p38 MAPK phosphorylation. XBP1s levels in total lysates are increased, but there is no detectable phosphorylation of XBP1s$^{Thr48}$ or XBP1s$^{Ser61}$, and no detectable XBP1s protein in the nucleus.

Figure 5A:
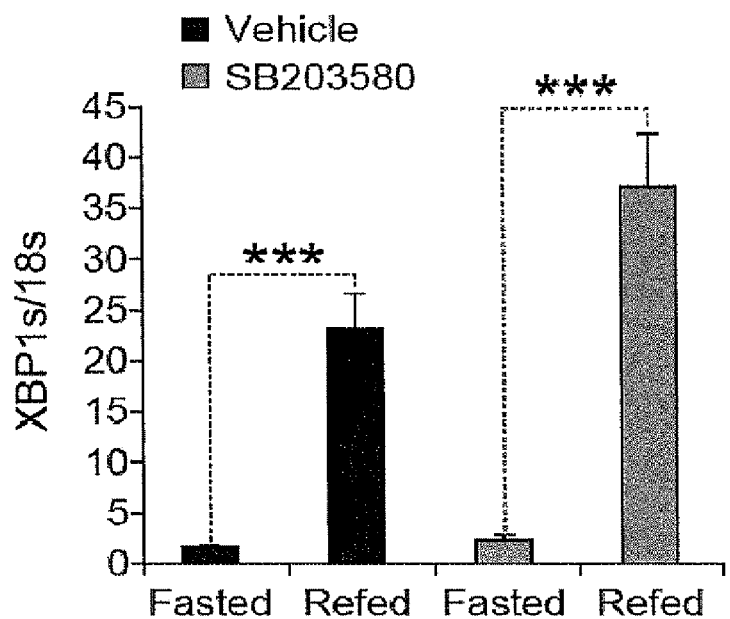
FIGS. 5A and 5B are bar graphs showing XBP1s (FIG. 5A) and GRP78 (FIG. 5B) mRNA levels at fasting and re-fed conditions in the livers of the mice either treated with vehicle (solid bars) or p38 MAPK inhibitor (SB203580) (shaded bars). Error bars are ±S.E.M. p<0.01, *p<0.001, N/S=Non-significant.
Figure 5B:
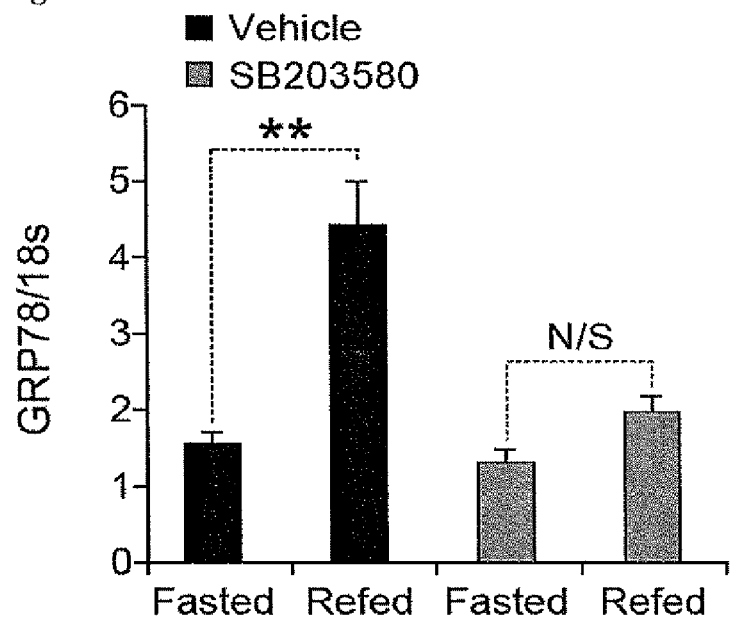

To examine whether inhibition of p38 MAPK signaling alone blocks XBP1s nuclear translocation in the mouse, 8-week-old wt C57BL6 lean male mice were treated for three days either with vehicle or with the p38 MAPK inhibitor (SB203580) (2 mg/kg/day, intraperitoneally), after which the mice were starved for 24 hours and refed for one hour. XBP1s nuclear levels significantly increased after refeeding in vehicle-treated control group. However, XBP1s nuclear translocation in the liver of SB203580-treated mice after re-feeding was completely absent. Analysis of ATF2, a p38 MAPK target, revealed a dramatic reduction in phosphorylation, indicating that SB203580 successfully blocked activation of p38 MAPK. XBP1s mRNA levels in the liver of re-fed mice that were either treated with vehicle or with the inhibitor, were significantly increased both in the vehicle-treated and SB203580-treated groups (FIG. 5A). Further analysis of mRNA levels of GRP78, which is an XBP1s-target gene, revealed that GRP78 expression was significantly increased in the vehicle-treated, but not in the inhibitor-treated group (FIG. 5B). When taken together, these results demonstrate that p38 MAPK signaling is critical for XBP1s nuclear translocation.

Example 9 p38 MAPK Activation Reduced ER Stress and Increases Insulin Sensitivity

Materials and Methods

Blood Glucose and Plasma Insulin Measurements

Mice were fasted for 6 h, after which their blood was analyzed for glucose measurement with a glucose meter (Bayer, Mishawaka, Ind.). For insulin analysis, mice were fasted for 24 h and plasma insulin were measured with an Ultra Sensitive Mouse Insulin ELISA kit from Crystal Chem (Downers Grove, Ill.).

Glucose Tolerance Test (GTT) and Insulin Tolerance Test (ITT)

For GTT analysis, mice were intraperitoneally injected with D-glucose (0.5 g/kg body weight for ob/ob, 2 g/kg body weight for XBP1$^{flox/flox}$ mouse) after an overnight fasting. Tail vein blood was collected at 0, 15, 30, 60, 90 and 120 min following glucose injection and blood glucose was measured with a glucose meter from Bayer. For ITT analysis, mice were fasted for 6 h (from 8 am to 2 pm) and intraperitoneally injected with recombinant human insulin (2 IU/kg for ob/ob mice) from Eli Lilly (Indianapolis, Ind.). Blood was taken from tail vein at 0, 15, 30, 60, 90 and 120 min after insulin injection and blood glucose was measured.

Real-Time Quantitative PCR

Total RNA was extracted and alyzed as described above. The primer sequences used were:

```
18S rRNA forward:
                                   (SEQ ID NO: 22)
5'-AGTCCCTGCCCTTTGTACACA-3';

18S rRNA reverse:
                                   (SEQ ID NO: 23)
5'-CGTTCCGAGGGCCTCACT-3';

ERdj4 forward:
                                   (SEQ ID NO: 24)
5'-CCCCAGTGTCAAACTGTACCAG-3';

ERdj4 reverse:
                                   (SEQ ID NO: 25)
5'-AGCGTTTCCAATTTTCCATAAATT-3';

GRP78 forward:
                                   (SEQ ID NO: 26)
5'-TCATCGGACGCACTTGGAA-3';
```

-continued

GRP78 reverse:
(SEQ ID NO: 27)
5'-CAACCACCTTGAATGGCAAGA-3';

G6Pase forward:
(SEQ ID NO: 28)
5'-CCGGTGTTTGAACGTCATCT-3';

G6Pase reverse:
(SEQ ID NO: 29)
5'-CAATGCCTGACAAGACTCCA-3';

PEPCK forward:
(SEQ ID NO: 30)
5'-ATCATCTTTGGTGGCCGTAG-3';

PEPCK reverse:
(SEQ ID NO: 31)
5'-ATCTTGCCCTTGTGTTCTGC-3';

PGC1α forward:
(SEQ ID NO: 32)
5'-TGATGTGAATGACTTGGATACAGACA-3';

PGC1α reverse:
(SEQ ID NO: 33)
5'-CAATGCCTGACAAGACTCCA-3';

Glucokinase forward:
(SEQ ID NO: 34)
5'-GAAAAGATCATTGGCGGAAA-3';

Glucokinase reverse:
(SEQ ID NO: 35)
5'-CCCAGAGTGCTCAGGATGTTAAG-3';

Blood Alanine Transaminase (ALT) and Aspartate Transaminase (AST) Measurements

The blood from mice before and after adenoviral injection was collected and blood ALT and AST levels were measured with ALT Color Endpoint Assay and AST Color Endpoint Assay kits from Bioo Scientific (Austin, Tex.) as instructed by provided manuals.

Results

Figure 11A:
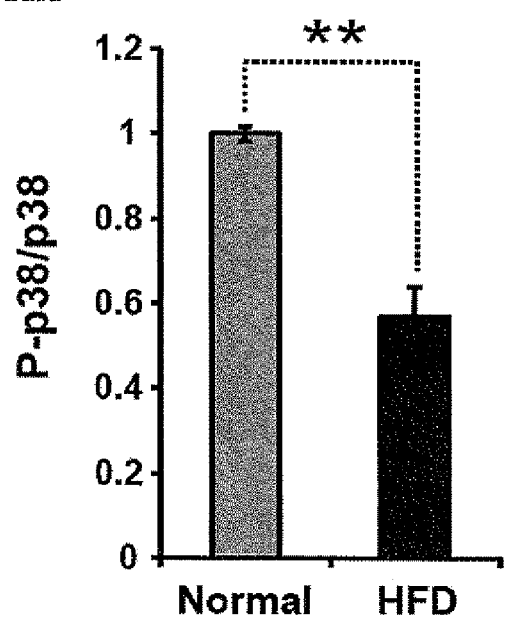
FIGS. 11A to 11C are bar graphs showing the ratio of phosphorylated p38 MAPK (P-p38) to total p38 protein in the liver (FIG. 11A), muscle (FIG. 11B), and adipose (WAT) (FIG. 11C) tissues from age-matched wild-type male mice under normal diet (shaded bars) or high fat diet (HFD) (sold bars) for 8 weeks. Error bars are ±S.E.M. *p<0.05, **p<0.01.
Figure 11B:
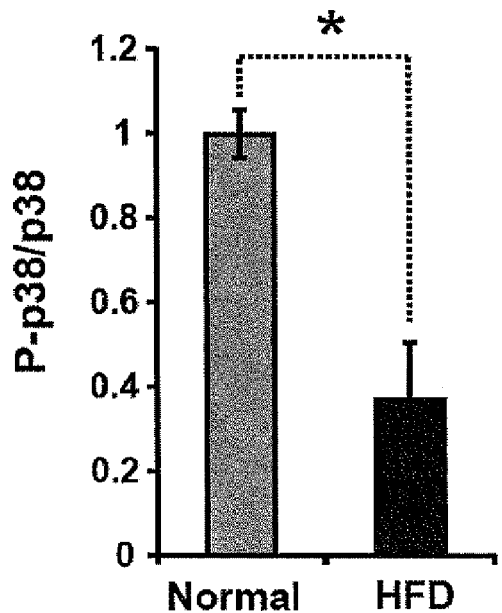
Figure 11C:
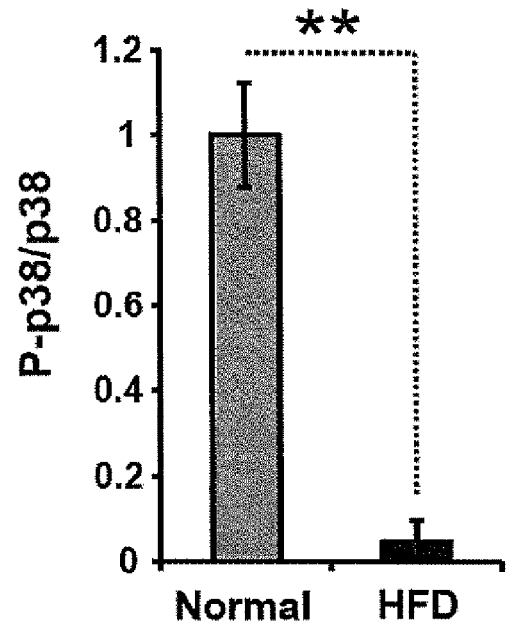

In addition to comparing fasting and refeeding states, basal p38 MAPK activity was also investigated in the liver, muscle and white adipose tissues of lean and obese mice. p38 MAPK phosphorylation was significantly reduced in the liver, muscle and adipose tissues of ob/ob and high fat diet-fed obese mice when compared to their lean counterparts (FIGS. 11A-11C). Previous observations also indicated that p38 MAPK phosphorylation was reduced in the liver tumors of the mice that were obese (Park, E. J., et al. (2010) Cell 140:197-208).

Figure 6A:
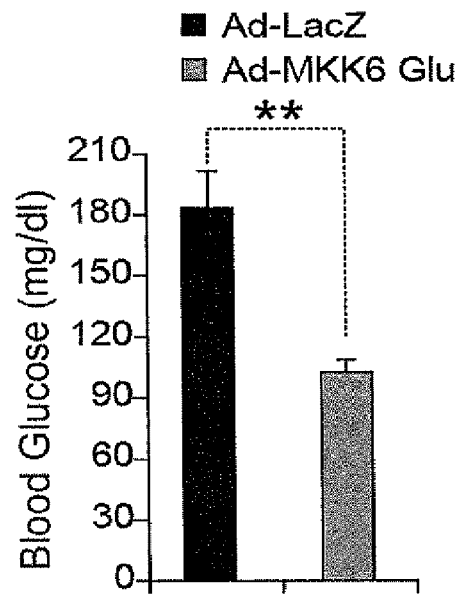
FIGS. 6A and 6B are bar graphs showing blood glucose (mg/dl) (FIG. 6A) and circulating insulin (ng/ml) (FIG. 6B) levels in eight-week-old male ob/ob mice infected with Ad-LacZ (solid bars) or Ad-MKK6Glu (shaded bars) ($8\times10^6$ pfu/g) via tail vein injection after six hours of fasting.
Figure 6B:
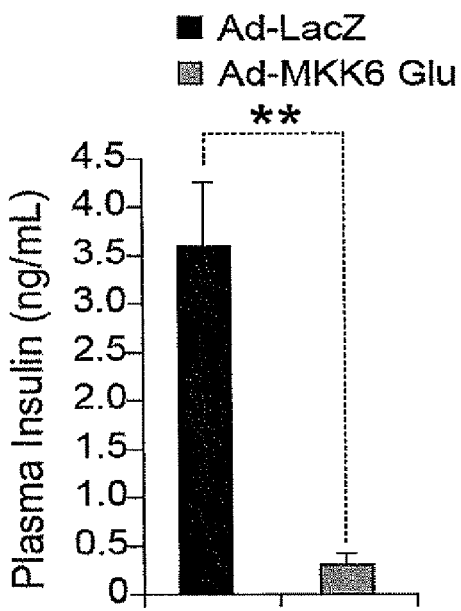
Figure 6C:
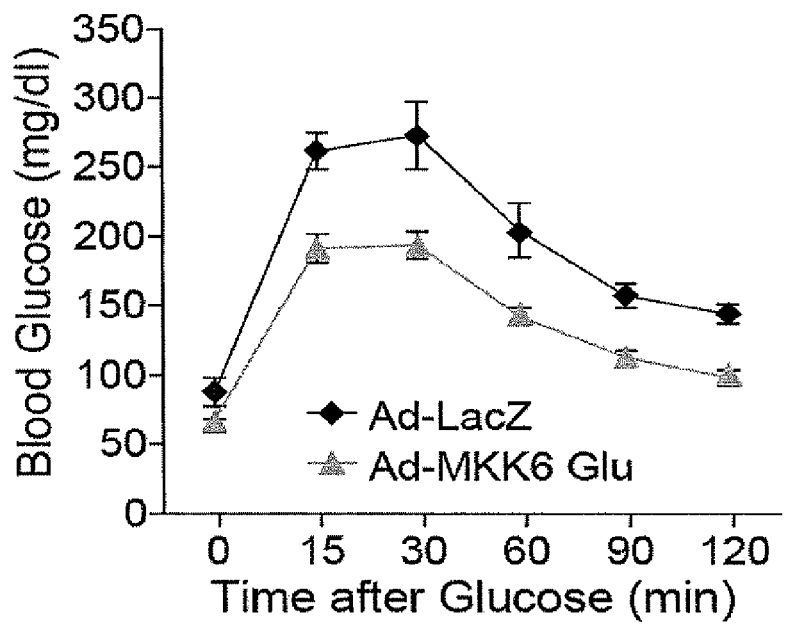
FIG. 6C is a graph showing blood glucose (mg/dl) levels in eight-week-old male ob/ob mice 0, 15, 30, 60, 90, or 120 minutes after intraperitoneal injection with glucose (0.5 g/kg) five days after injection with Ad-LacZ (♦) or Ad-MKK6Glu (▲).
Figure 6D:
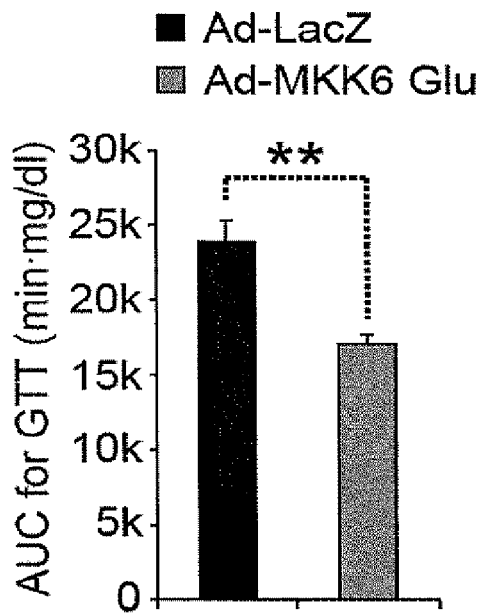
FIG. 6D is a bar graph showing area under the curve (AUC) (min-mg/dl) of data in FIG. 6C for mice injected with Ad-LacZ (solid bar) or Ad-MKK6Glu (shaded bar).
Figure 6E:
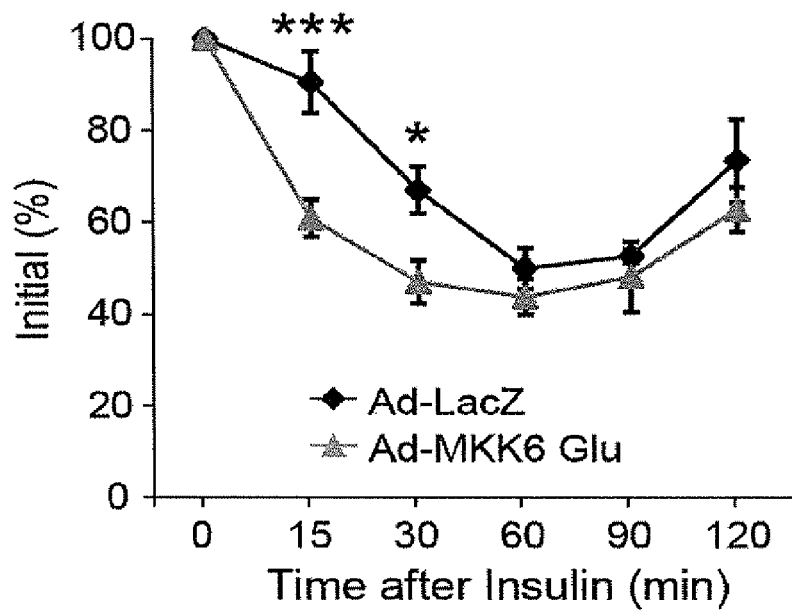
FIG. 6E is a graph showing insulin levels (% change) in eight-week-old male ob/ob mice 0, 15, 30, 60, 90, or 120 minutes after intraperitoneal injection with insulin (2 IU/kg) three days after injection with Ad-LacZ (♦) or Ad-MKK6Glu (▲).

To determine whether reactivation of p38 MAPK in the liver of obese and diabetic mice would increase XBP1s phosphorylation, reduce ER stress, increase glucose tolerance and reduce blood glucose levels, MKK6Glu was cloned into an adenoviral vector, and adenovirus particles (Ad-MKK6Glu) produced. Infection of cells with Ad-MKK6Glu led to a significant upregulation in MKK6Glu levels when compared with the Ad-LacZ-infected control cells. Next, eight-week-old ob/ob mice were injected though the tail vein with $8\times10^6$ PFU/g of Ad-MKK6Glu, or of Ad-LacZ. Six-hour fasting blood glucose levels on post-injection day three were significantly reduced in the Ad-MKK6Glu-injected group compared with the Ad-LacZ-injected control mice (FIG. 6A). A significant reduction was noted in the circulating insulin levels of the MKK6Glu overexpressing ob/ob mice, indicating that insulin sensitivity is increased (FIG. 6B). Moreover, as documented by glucose tolerance test, the glucose disposal rate in the Ad-MKK6Glu-injected group was significantly enhanced when compared with the Ad-LacZ-injected group (FIGS. 6C-6D). Performance of insulin tolerance test (ITT) at post-injection day three also revealed an increased insulin sensitivity in the Ad-MKK6Glu-injected group (FIG. 6E).

Figure 6F:
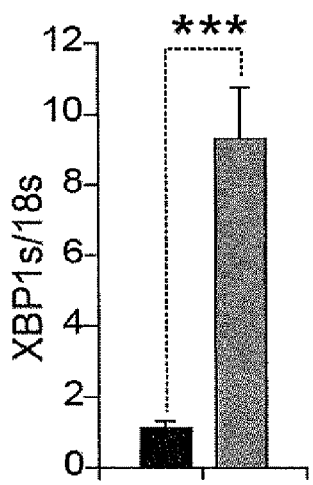
FIGS. 6F to 6H are bar graphs showing mRNA levels (normalized to 18s) of XBP1s (FIG. 6F), GRP78 (FIG. 6G) and Erdj4 (FIG. 6H) in the livers of Ad-LacZ-injected (solid bars) or Ad-MKK6Glu-injected (shaded bars) ob/ob mice.
Figure 6G:
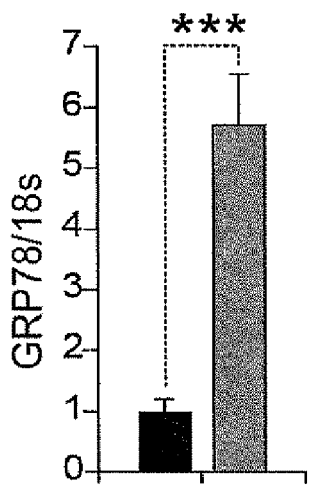
Figure 6H:
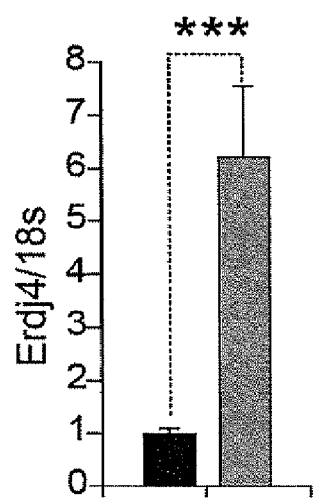

Analysis of liver samples from Ad-LacZ and Ad-MKK6Glu-injected ob/ob mice documented that p38 MAPK phosphorylation and downstream signaling were significantly increased in the MKK6Glu expressing ob/ob livers. Furthermore, XBP1s total protein levels, nuclear protein levels, and Thr48 and Ser61 phosphorylations were markedly increased when MKK6Glu was expressed in the liver of ob/ob mice. mRNA levels of XBP1s, and expression of XBP1s-target genes (GRP78 and Erdj4), were also significantly elevated, indicating increased XBP1s mRNA stability and activity (FIGS. 6F-6H). IRE1α phosphorylation levels, which are indicative of ER stress, was dramatically reduced in MKK6Glu-expressing ob/ob livers, showing that ER stress is indeed reduced by activation of p38 MAPK pathway.

Figure 6I:
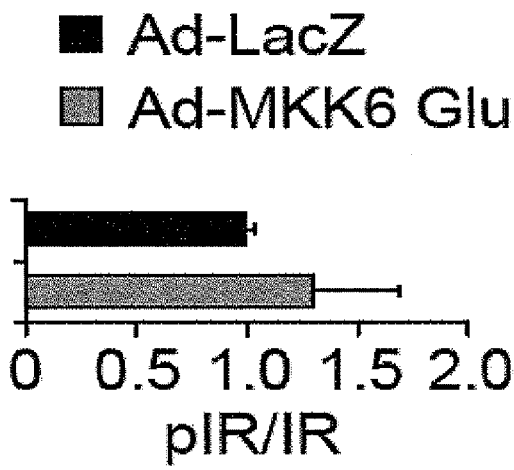
FIGS. 6I to 6K are bar graphs showing the ratio of phosphorylated IR (FIG. 6I), IRS1 (FIG. 6J), and Akt$^{Thr308}$ (FIG. 6K) to total protein in Ad-LacZ-injected (solid bars) or Ad-MKK6Glu-injected (shaded bars) ob/ob mice starved for six hours on post injection day seven and subsequently infused with insulin (0.75 IU/kg) through portal vein.
Figure 6J:
Figure 6K:
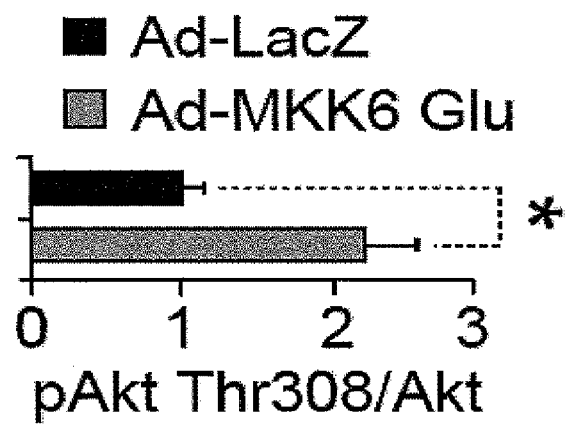
Figure 6L:
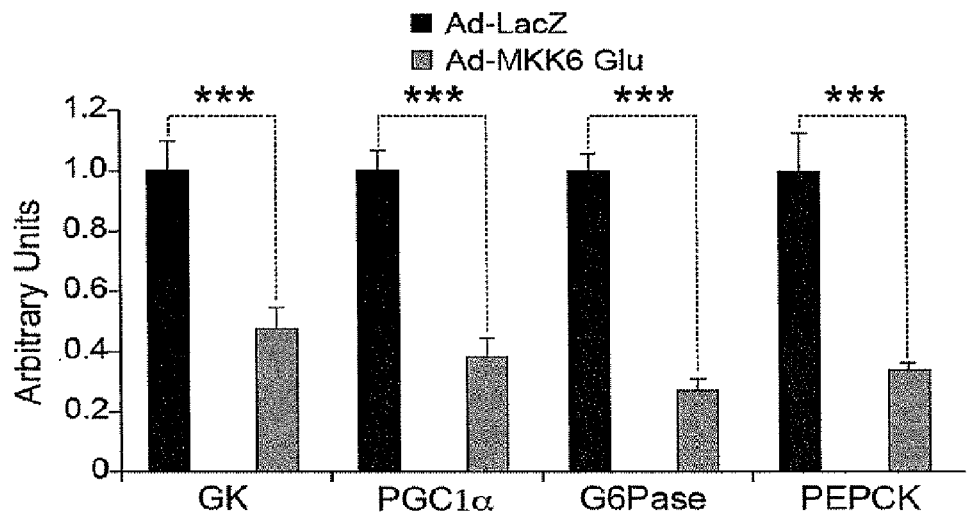
FIG. 6L is a bar graph showing mRNA levels (arbitrary units) of GK (first and second bars), PGC1α (third and fourth bars), G6Pase (fifth and sixth bars), and PEPCK (seventh and eighth bars) in the livers of ob/ob mice injected with Ad-LacZ (solid bars) or Ad-MKK6Glu (shaded bars). Error bars are ±S.E.M. *p=0.05, p<0.01, *p<0.001.

To investigate whether insulin sensitivity is altered in the livers of Ad-MKK6Glu-injected ob/ob mice when compared with the controls, insulin (0.75 IU/kg) was infused though portal vein into the livers of the Ad-LacZ-injected and Ad-MKK6Glu-injected ob/ob mice on post-injection day seven, and the activation of IR, IRS1 and Akt analyzed. No differences were seen between the two groups (saline versus insulin infusion) in terms of insulin-stimulated tyrosine phosphorylation of IR but there were significant increases in IRS1 tyrosine and $Akt^{Thr308}$ phosphorylations (FIGS. 6I-6K). Furthermore, expression levels of genes (such as GK, G6Pase, PEPCK and PGC1α), which are involved in the glucose homeostasis, revealed a significant down regulation when MKK6Glu was expressed in the livers of the ob/ob mice (FIG. 6L).

Figure 12A:
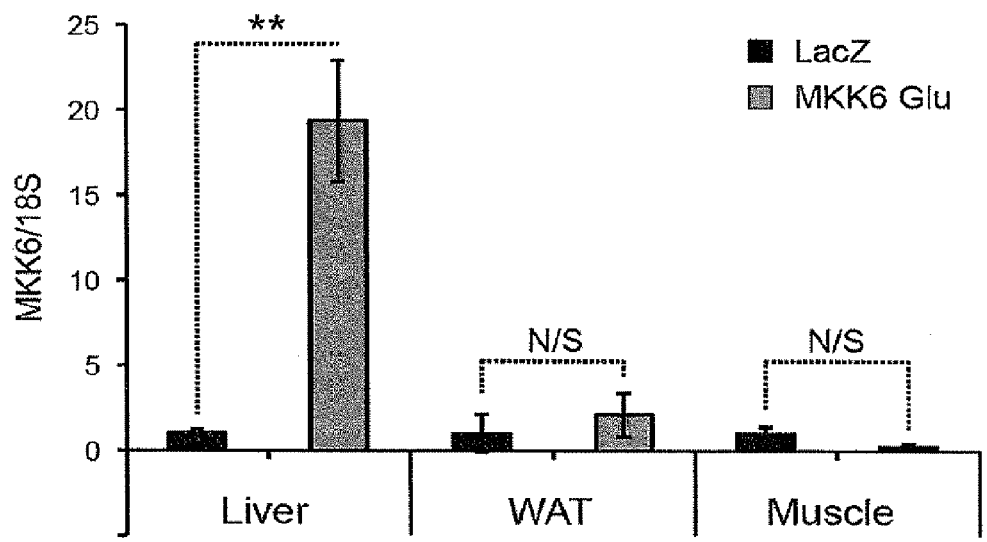
FIG. 12A is a bar graph showing mRNA level (normalized to 18S) of MKK6 the liver (bars 1-2), adipose tissue (WAT) (bars 3-4), and muscle (bars 5-6) of 8-week-old male ob/ob mice injected with 8×10$^6$ pfu/g Ad-LacZ (solid bar) or Ad-MKK6Glu (shaded bar) through the tail vein.
Figure 12B:
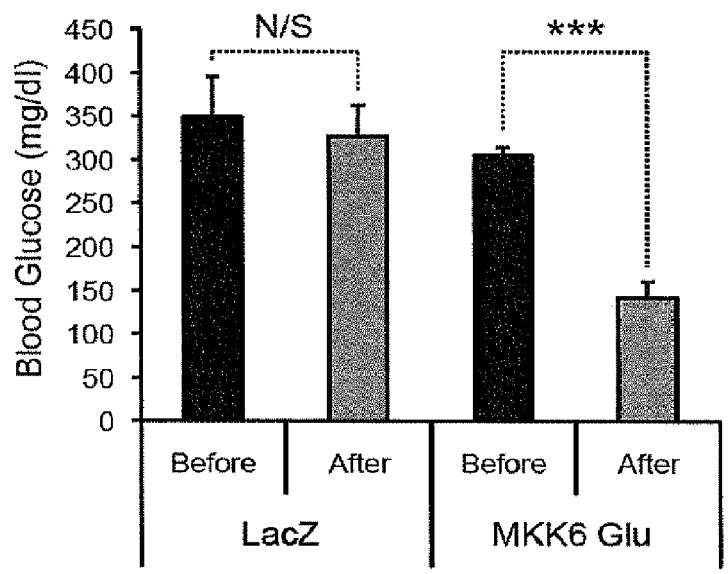
FIGS. 12B and 12C are bar graphs showing blood glucose levels (mg/dl) (FIG. 12B) and body weight (g) of 8-week-old male ob/ob mice before (solid bars) and 4 days after (shaded bars) injection with Ad-LacZ (bars 1-2) or Ad-MKK6Glu (bars 3-4).
Figure 12C:
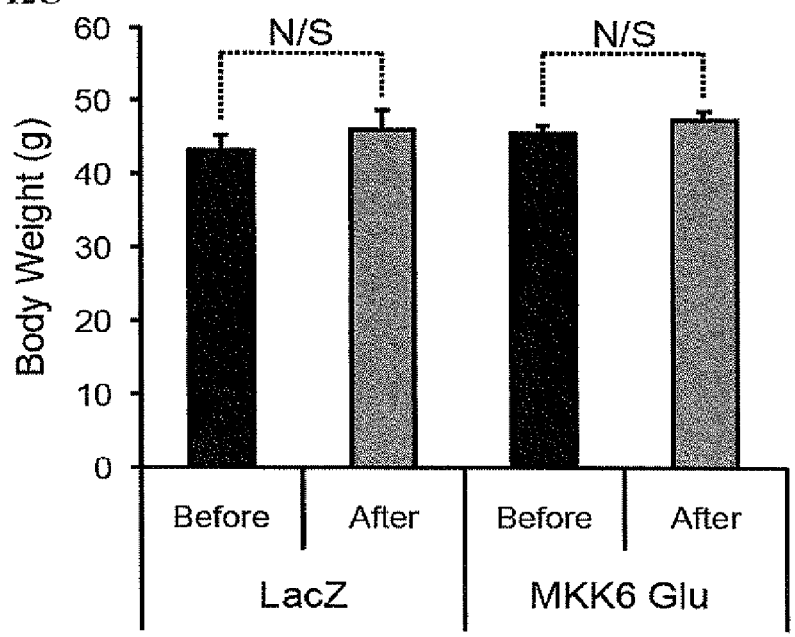
Figure 12D:
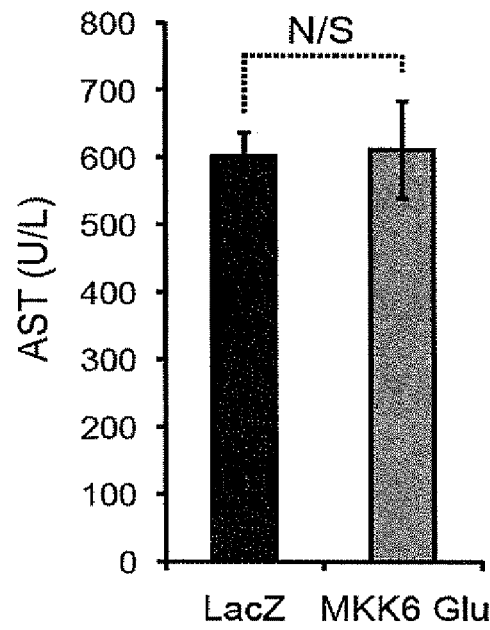
FIGS. 12D and 12E are bar graphs showing aspartate transaminase (AST) (FIG. 12D) and alanine transaminase (ALT) (FIG. 12E) levels in the blood of mice injected with Ad-LacZ (solid bar) or Ad-MKK6Glu (shaded bar). Error bars are ±S.E.M. p<0.01, *p<0.001, N/S =non-significant.
Figure 12E:
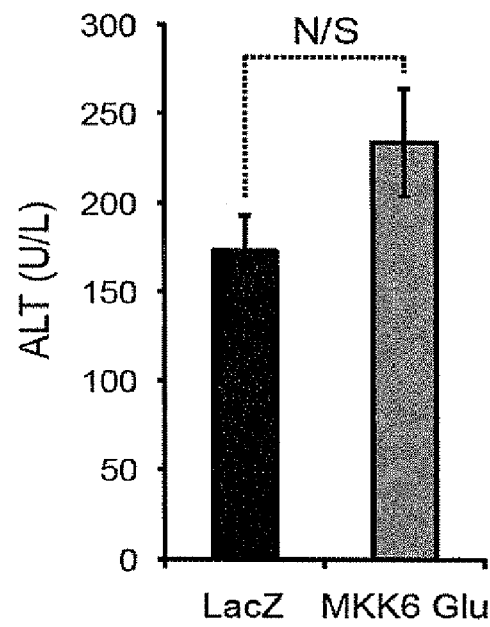

The extent of MKK6Glu expression in other tissues such as muscle and white adipose tissue (WAT) was also determined after tail vein injection of the adenoviruses. As shown in FIG. 12A, the only significant increase in the expression of MKK6Glu was observed in the liver. In addition LacZ expression in the liver by tail vein injection of Ad-LacZ did not affect the blood glucose levels of ob/ob mice (FIG. 12B). Furthermore tail vein injection of either Ad-LacZ or Ad-MKK6Glu did not alter the bodyweight and also did not lead to increase in liver function tests such as AST and ALT (FIGS. 12C-12D).

Example 10

MKK6Glu-Mediated Enhancement of Glucose Homeostasis is XBP1s Dependent

Materials and Methods
Results

Figure 7A:
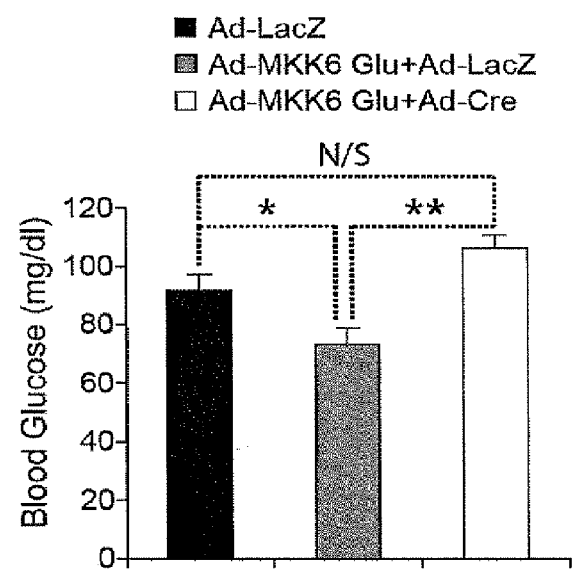
FIG. 7A is a bar graph showing fasting blood glucose levels (mg/dl) 13 days post-injection in XBP1$^{flox/flox}$ mice fed a high fat diet (HFD) for 16 weeks and injected with 1) Ad-LacZ ($1.58\times10^8$ pfu/g) (solid bar), 2) Ad-MKK6Glu ($0.08\times10^8$ pfu/g) and Ad-LacZ ($1.5\times10^8$ pfu/g) (shaded bar), or 3) Ad-MKK6Glu ($0.08\times10^8$ pfu/g) and Ad-Cre ($1.5\times10^8$ pfu/g) (open bar) though the tail vein.
Figure 7B:
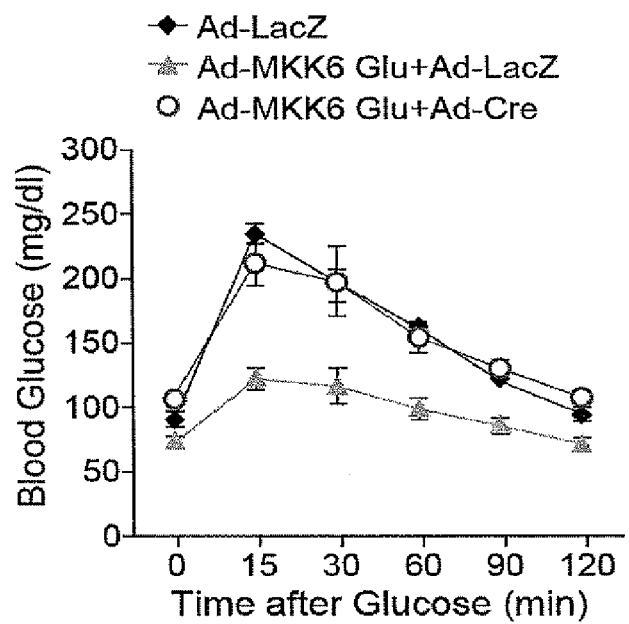
FIG. 7B is a graph showing blood glucose levels (mg/dl) in XBP1$^{flox/flox}$ mice at 0, 15, 30, 60, 90, 120 min after intraperitoneal glucose (1 g/kg) injection with 1) Ad-LacZ ($1.58\times10^8$ pfu/g) (♦), 2) Ad-MKK6Glu ($0.08\times10^8$ pfu/g) and Ad-LacZ ($1.5\times10^8$ pfu/g) (▲), or 3) Ad-MKK6Glu ($0.08\times10^8$ pfu/g) and Ad-Cre ($1.5\times10^8$ pfu/g) (●).
Figure 7C:
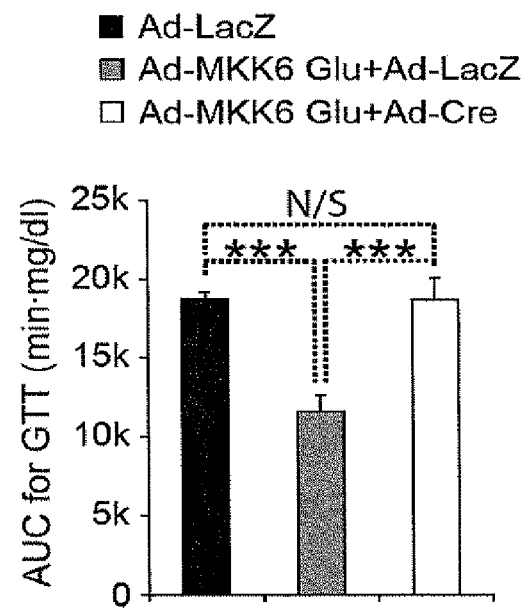
FIG. 7C is a bar graph showing area under the curve (AUC) (min-mg/dl) of data in FIG. 7B for mice injected with 1) Ad-LacZ ($1.58\times10^8$ pfu/g) (solid bar), 2) Ad-MKK6Glu ($0.08\times10^8$ pfu/g) and Ad-LacZ ($1.5\times10^8$ pfu/g) (shaded bar), or 3) Ad-MKK6Glu ($0.08\times10^8$ pfu/g) and Ad-Cre ($1.5\times10^8$ pfu/g) (open bar).
Figure 7D:
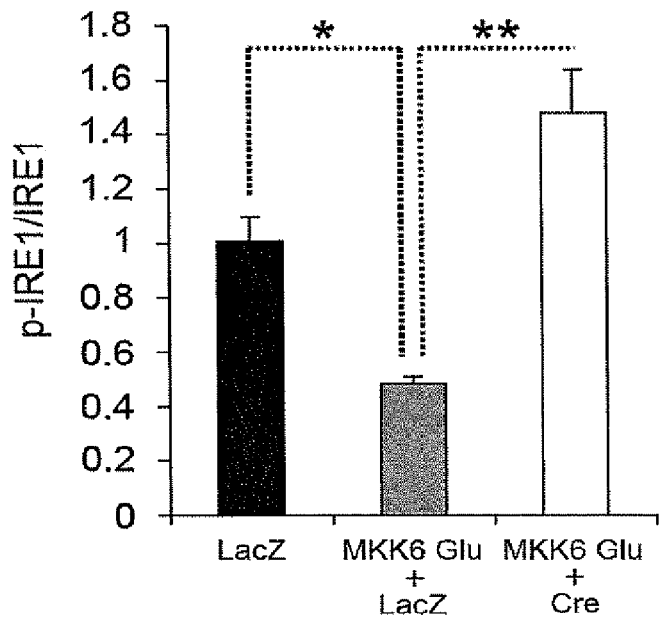
FIG. 7D is a bar graph showing the ratio of p-IRE1$^{Ser724}$ to total IRE1 levels in mice injected with 1) Ad-LacZ ($1.58\times10^8$ pfu/g) (solid bar), 2) Ad-MKK6Glu ($0.08\times10^8$ pfu/g) and Ad-LacZ ($1.5\times10^8$ pfu/g) (shaded bar), or 3) Ad-MKK6Glu ($0.08\times10^8$ pfu/g) and Ad-Cre ($1.5\times10^8$ pfu/g) (open bar).
Figure 7E:
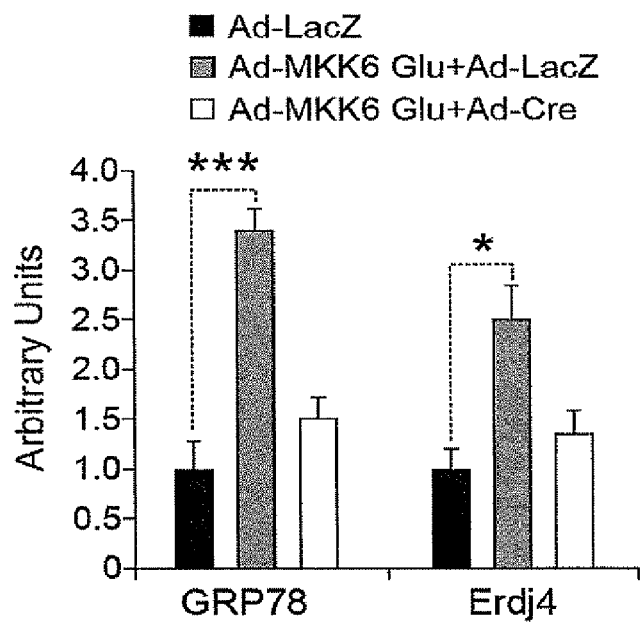
FIGS. 7E and 7F are bar graphs showing mRNA levels (arbitrary units) of GRP78 (FIG. 7E, bars 1-3), Erdj4 (FIG. 7E, bars 4-6), GK (FIG. 7F, bars 1-3), G6Pase (FIG. 7F, bars 4-6), PEPCK (FIG. 7F, bars 7-9), and PGC1α (FIG. 7F, bars 10-12) in the livers of mice injected with 1) Ad-LacZ ($1.58\times10^8$ pfu/g) (solid bar), 2) Ad-MKK6Glu ($0.08\times10^8$ pfu/g) and Ad-LacZ ($1.5\times10^8$ pfu/g) (shaded bar), or 3) Ad-MKK6Glu ($0.08\times10^8$ pfu/g) and Ad-Cre ($1.5\times10^8$ pfu/g) (open bar). Error bars are ±S.E.M. *p<0.05, p<0.01, *p<0.001.
Figure 7F:
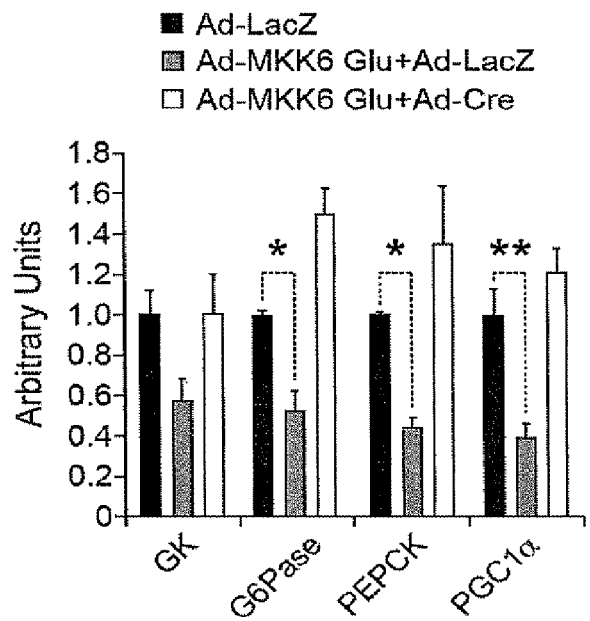

To determine the role of XBP1s in MKK6Glu-mediated enhancement of glucose homeostasis MKK6Glu was overexpressed in the liver of 16-week high fat diet (HFD)-fed XBP1$^{flox/flox}$ mice, while XBP1 was simultaneously depleted with use of an adenovirus that expresses Cre recombinase (Ad-Cre). The first group of mice were injected with Ad-LacZ ($1.58\times10^8$ pfu/g), second group with Ad-MKK6Glu ($0.08\times10^8$ pfu/g) plus Ad-LacZ ($1.5\times10^8$ pfu/g) and the third group with Ad-MKK6Glu ($0.08\times10^8$ pfu/g) and Ad-Cre (1.5×10⁸ pfu/g). In parallel with the results obtained from the experiments on the ob/ob mice, injection of Ad-MKK6Glu into the XBP1$^{flox/flox}$ mice led to a significant decrease in blood glucose levels (FIG. 7A). However, injection of Ad-Cre together with Ad-MKK6Glu completely eliminated the effect of MKK6Glu on blood glucose levels, indicating that XBP1s plays a major role in the improved glucose homeostasis mediated by MKK6Glu expression in the liver (FIG. 7A). Next, a glucose tolerance test was performed on post injection day 15. Glucose disposal from circulation was significantly enhanced in the MKK6Glu-expressing XBP1$^{flox/flox}$ mice, while depletion of XBP1 in the MKK6Glu-expressing mice eliminated this effect (FIGS. 7B-7C).

p38 MAPK activation, MKK6 and XBP1s nuclear levels was also analyzed. p38 MAPK activation as well as MKK6 was significantly increased in all the MKK6Glu expressing groups. XBP1s nuclear translocation was significantly increased in the MKK6Glu expressing group, but completely eliminated in the MKK6Glu plus Cre recombinase-expressing group. These results demonstate that XBP1s is successfully depleted by Cre recombinase expression in the liver of XBP1$^{flox/flox}$ mice. Furthermore, analysis of IRE1$^{Ser724}$ phosphorylation revealed a significant down regulation in the MKK6Glu expressing group, and this downregulation was abolished in the MKK6Glu plus Cre recombinase expressing group (FIG. 7D). Next, the expression of chaperones was determined. MKK6Glu expression led to a significant upregulation in the expression of Erdj4 and GRP78 but this effect was diminished in the XBP1s-depleted group (FIG. 7E). Finally, analysis of G6Pase, PEPCK and PGC1α mRNA levels revealed that MKK6-mediated down regulation of these genes were lost in the XBP1s-depleted mice (FIG. 7F). There was a slight decrease in GK levels but not at significant levels (FIG. 7F).

Example 11

Figure 8A:
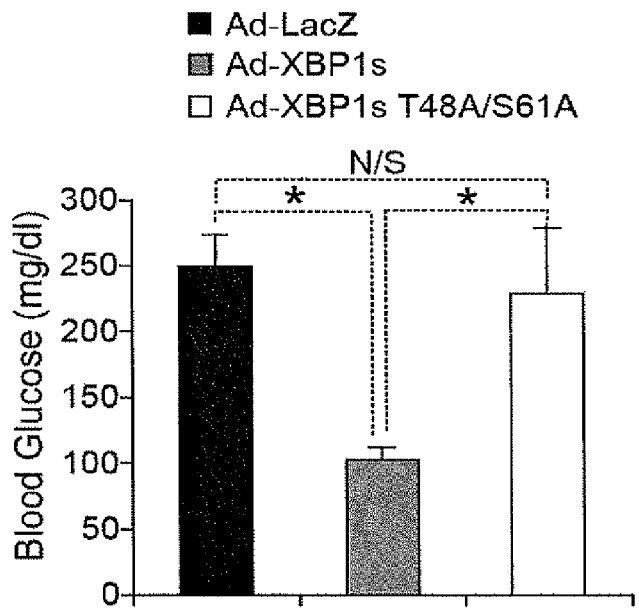
FIG. 8A is a bar graphs showing six-hour fasting blood glucose levels (mg/dl) three days after ob/ob mice were injected with 1) Ad-LacZ (solid bar), 2) Ad-XBP1s (shaded bar), or 3) Ad-XBP1s-T48A/S61A (open bar) via the tail vein.
Figure 8B:
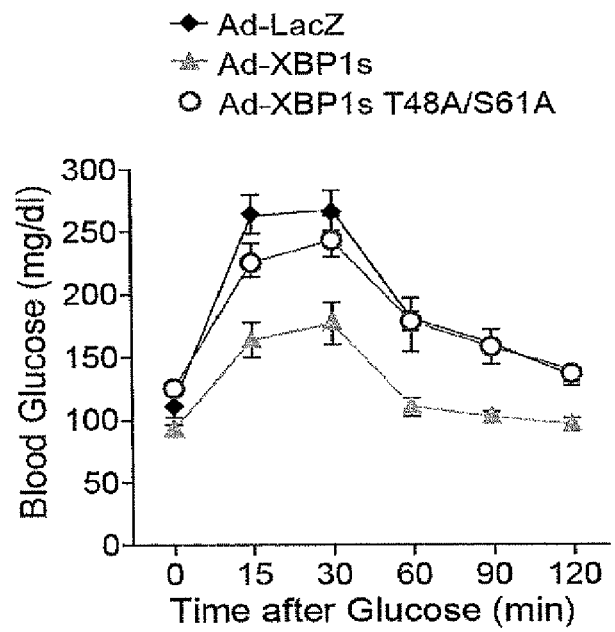
FIG. 8B is a graph showing blood glucose levels (mg/dl) 0, 15, 30, 60, 90, or 120 minutes after intraperitoneal injection with glucose (0.5 g/kg) and five days after injection with 1) Ad-LacZ (♦), 2) Ad-XBP1s (▲), or 3) Ad-XBP1s-T48A/S61A (●) via the tail vein.
Figure 8C:
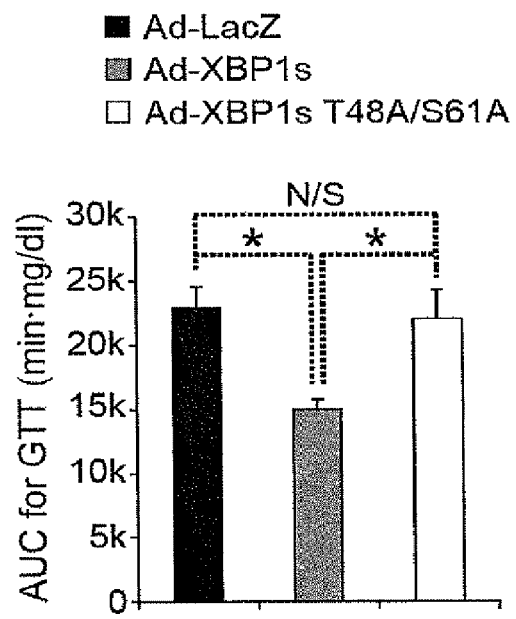
FIG. 8C is a bar graph showing area under the curve (AUC) (min-mg/dl) of data in FIG. 8B for mice injected with 1) Ad-LacZ (solid bar), 2) Ad-XBP1s (shaded bar), or 3) Ad-XBP1s-T48A/S61A (open bar).
Figure 8D:
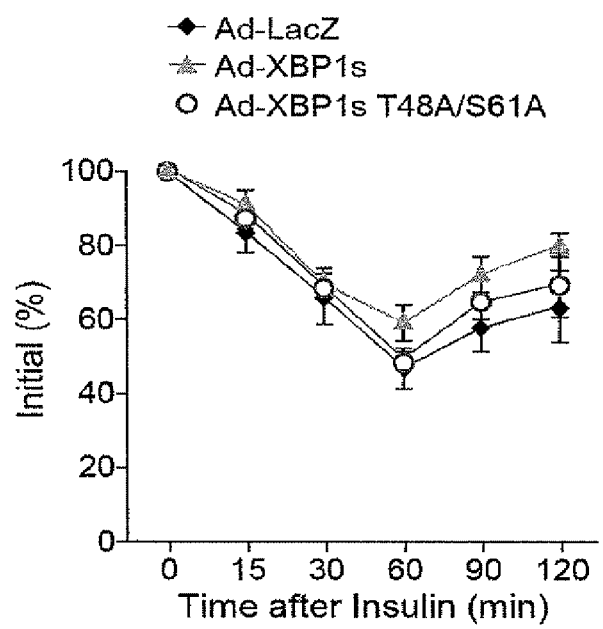
FIG. 8D is a graph showing insulin levels (% change) in ob/ob mice 0, 15, 30, 60, 90, or 120 minutes after intraperitoneal injection with insulin seven days after injection with 1) Ad-LacZ (♦), 2) Ad-XBP1s (▲), or 3) Ad-XBP1s-T48A/S61A (●).

XBP1s Phosphorylation Required for Nuclear Translocation and Effect on Glucose Tolerance Overexpression of XBP1s in the liver of obese mice increases glucose tolerance and significantly reduce the blood glucose levels (Zhou, Y., et al. (2011) *Nature Med* 17(3):356-65). Therefore, the T48A/S61A double mutant XBP1s, when expressed in the liver of obese mice, should not translocate to the nucleus and should not have any effect on glucose homeostasis. To confirm, eight-week-old male ob/ob mice were injected either with Ad-LacZ (3.6×10⁷ pfu/g) or Ad-XBP1s (3.6×10⁷ pfu/g) or Ad-XBP1s T48A/S61A (3.6×10⁷ pfu/g). Analysis of blood glucose levels on post-injection day three showed that blood glucose of Ad-XBP1s-injected ob/ob mice were at euglycemia levels (FIG. 8A). However, expression of T48A/S61A mutant XBP1s had no effect on blood glucose levels (FIG. 8A). Performance of GTT on post-injection day five revealed that mutation of Thr48 and Ser61 diminished the ability of XBP1s to enhance glucose tolerance (FIGS. 8B-8C). In parallel with recent observations (Zhou, Y., et al. (2011) *Nature Med* 17(3):356-65) medium levels of XBP1s expression in the liver did not alter insulin tolerance (FIG. 8D).

Figure 8E:
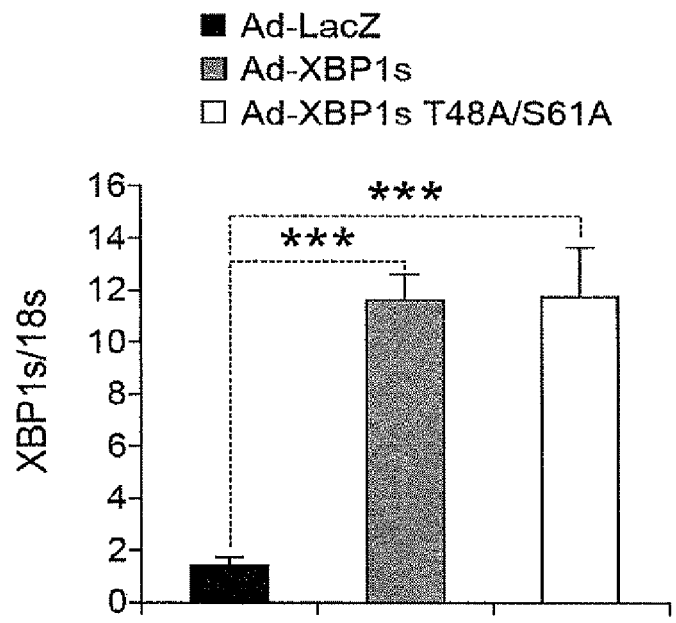
FIGS. 8E to 8G are bar graphs showing mRNA levels (normalized to 18S) of XBP1s (FIG. 8E), GRP78 (FIG. 8F) and Erdj4 (FIG. 8G) in livers of mice injected with 1) Ad-LacZ (solid bar), 2) Ad-XBP1s (shaded bar), or 3) Ad-XBP1s-T48A/S61A (open bar). Error bars are ±S.E.M. *p<0.05, p<0.01, *p<0.001.
Figure 8F:
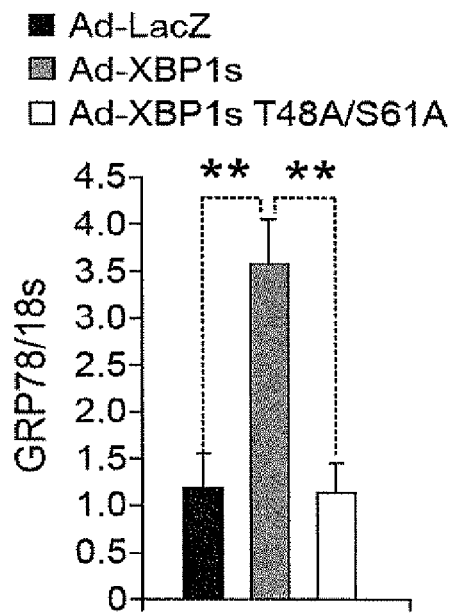
Figure 8G:
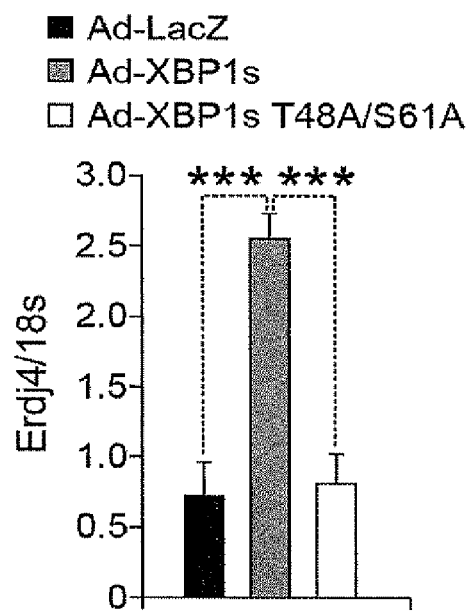

Nuclear levels of XBP1s were significantly increased in the livers of Ad-XBP1s-injected group, but there were no detectable mutant XBP1s in the nuclear fractions of the livers of Ad-XBP1s T48A/S61A-injected group. Analysis of total protein and mRNA levels of XBP1s and XBP1s T48A/S61A demonstrated that both XBP1s' were expressed at similar amounts in the liver (FIG. 8E). Furthermore, upregulation of the chaperones, such as Erdj4 and GRP78, seen after XBP1s expression, were diminished in the livers of ob/ob mice that were expressing the mutant XBP1s (FIG. 8F-8G). These results provide further evidence that phosphorylation of XBP1s on T48/S61 is imperative for its function in vivo.

We claim:

1. A method of reducing blood glucose in a subject, comprising administering to the subject a pharmaceutical composition comprising a specific activator of X-box binding protein 1 (XBP1) in an effective amount to reduce blood glucose in the subject, wherein the specific activator increases phosphorylation of XBP1on Thr48 and Ser61.

2. The method of claim 1, wherein the subject has type II diabetes.

3. The method of claim 1, wherein the subject is obese.

4. The method of claim 1, wherein the pharmaceutical composition is administered at a non-toxic dosage, wherein an effective amount of the specific activator is maintained in the subject for a period of at least 5 days.

5. The method of claim 4, wherein the pharmaceutical composition is administered for a period of at least 10 days.

6. The method of claim 4, wherein the pharmaceutical composition is an extended release formulation.

* * * * *

SEQUENCE LISTING

```
<160> NUMBER OF SEQ ID NOS: 35

<210> SEQ ID NO 1
<211> LENGTH: 454
<212> TYPE: PRT
<213> ORGANISM: Unknown
<220> FEATURE:
<223> OTHER INFORMATION: Synthetic His-TF tag (6XHis + TF tag + 3C
      protease cleavage site)

<400> SEQUENCE: 1

Met Asn His Lys Val His His His His His His Met Gln Val Ser Val
1               5                   10                  15

Glu Thr Thr Gln Gly Leu Gly Arg Arg Val Thr Ile Thr Ile Ala Ala
            20                  25                  30

Asp Ser Ile Glu Thr Ala Val Lys Ser Glu Leu Val Asn Val Ala Lys
        35                  40                  45

Lys Val Arg Ile Asp Gly Phe Arg Lys Gly Lys Val Pro Met Asn Ile
    50                  55                  60

Val Ala Gln Arg Tyr Gly Ala Ser Val Arg Gln Asp Val Leu Gly Asp
65                  70                  75                  80

Leu Met Ser Arg Asn Phe Ile Asp Ala Ile Ile Lys Glu Lys Ile Asn
                85                  90                  95

Pro Ala Gly Ala Pro Thr Tyr Val Pro Gly Glu Tyr Lys Leu Gly Glu
```

```
              100                 105                 110
Asp Phe Thr Tyr Ser Val Glu Phe Glu Val Tyr Pro Glu Val Glu Leu
            115                 120                 125

Gln Gly Leu Glu Ala Ile Glu Val Glu Lys Pro Ile Val Glu Val Thr
        130                 135                 140

Asp Ala Asp Val Asp Gly Met Leu Asp Thr Leu Arg Lys Gln Gln Ala
145                 150                 155                 160

Thr Trp Lys Glu Lys Asp Gly Ala Val Glu Ala Glu Asp Arg Val Thr
                165                 170                 175

Ile Asp Phe Thr Gly Ser Val Asp Gly Glu Glu Phe Glu Gly Gly Lys
            180                 185                 190

Ala Ser Asp Phe Val Leu Ala Met Gly Gln Gly Arg Met Ile Pro Gly
        195                 200                 205

Phe Glu Asp Gly Ile Lys Gly His Lys Ala Gly Glu Glu Phe Thr Ile
    210                 215                 220

Asp Val Thr Phe Pro Glu Glu Tyr His Ala Glu Asn Leu Lys Gly Lys
225                 230                 235                 240

Ala Ala Lys Phe Ala Ile Asn Leu Lys Lys Val Glu Glu Arg Glu Leu
                245                 250                 255

Pro Glu Leu Thr Ala Glu Phe Ile Lys Arg Phe Gly Val Glu Asp Gly
            260                 265                 270

Ser Val Glu Gly Leu Arg Ala Glu Val Arg Lys Asn Met Glu Arg Glu
        275                 280                 285

Leu Lys Ser Ala Ile Arg Asn Arg Val Lys Ser Gln Ala Ile Glu Gly
    290                 295                 300

Leu Val Lys Ala Asn Asp Ile Asp Val Pro Ala Ala Leu Ile Asp Ser
305                 310                 315                 320

Glu Ile Asp Val Leu Arg Arg Gln Ala Ala Gln Arg Phe Gly Gly Asn
                325                 330                 335

Glu Lys Gln Ala Leu Glu Leu Pro Arg Glu Leu Phe Glu Glu Gln Ala
            340                 345                 350

Lys Arg Arg Val Val Val Gly Leu Leu Leu Gly Glu Val Ile Arg Thr
        355                 360                 365

Asn Glu Leu Lys Ala Asp Glu Glu Arg Val Lys Gly Leu Ile Glu Glu
    370                 375                 380

Met Ala Ser Ala Tyr Glu Asp Pro Lys Glu Val Ile Glu Phe Tyr Ser
385                 390                 395                 400

Lys Asn Lys Glu Leu Met Asp Asn Met Arg Asn Val Ala Leu Glu Glu
                405                 410                 415

Gln Ala Val Glu Ala Val Leu Ala Lys Ala Lys Val Thr Glu Lys Glu
            420                 425                 430

Thr Thr Phe Asn Glu Leu Met Asn Gln Gln Ala Ser Ala Gly Leu Glu
        435                 440                 445

Val Leu Phe Gln Gly Pro
    450

<210> SEQ ID NO 2
<211> LENGTH: 21
<212> TYPE: DNA
<213> ORGANISM: Artificial Sequence
<220> FEATURE:
<223> OTHER INFORMATION: Synthetic Primer

<400> SEQUENCE: 2
agtccctgcc ctttgtacac a                                          21
```

<210> SEQ ID NO 3
<211> LENGTH: 18
<212> TYPE: DNA
<213> ORGANISM: Artificial Sequence
<220> FEATURE:
<223> OTHER INFORMATION: Synthetic Primer

<400> SEQUENCE: 3
cgttccgagg gcctcact                                                    18

<210> SEQ ID NO 4
<211> LENGTH: 22
<212> TYPE: DNA
<213> ORGANISM: Artificial Sequence
<220> FEATURE:
<223> OTHER INFORMATION: Synthetic Primer

<400> SEQUENCE: 4
ggtctgctga gtccgcagca gg                                               22

<210> SEQ ID NO 5
<211> LENGTH: 19
<212> TYPE: DNA
<213> ORGANISM: Artificial Sequence
<220> FEATURE:
<223> OTHER INFORMATION: Synthetic Primer

<400> SEQUENCE: 5
aggcttggtg tatacatgg                                                   19

<210> SEQ ID NO 6
<211> LENGTH: 37
<212> TYPE: DNA
<213> ORGANISM: Artificial Sequence
<220> FEATURE:
<223> OTHER INFORMATION: Synthetic Primer

<400> SEQUENCE: 6
ttaagggtac cggcgccatg tctcagtcga aaggcaa                               37

<210> SEQ ID NO 7
<211> LENGTH: 37
<212> TYPE: DNA
<213> ORGANISM: Artificial Sequence
<220> FEATURE:
<223> OTHER INFORMATION: Synthetic Primer

<400> SEQUENCE: 7
ttaaggcggc cgcttatcat tagtctccaa gaatcag                               37

<210> SEQ ID NO 8
<211> LENGTH: 19
<212> TYPE: DNA
<213> ORGANISM: Artificial Sequence
<220> FEATURE:
<223> OTHER INFORMATION: Synthetic targeting sequence

<400> SEQUENCE: 8
tgaatggaag tatgacgtt                                                   19

<210> SEQ ID NO 9
<211> LENGTH: 19
<212> TYPE: DNA
<213> ORGANISM: Artificial Sequence
<220> FEATURE:

<223> OTHER INFORMATION: Synthetic targeting sequence

<400> SEQUENCE: 9
agtggttatg ggaaagtat                                                   19

<210> SEQ ID NO 10
<211> LENGTH: 19
<212> TYPE: DNA
<213> ORGANISM: Artificial Sequence
<220> FEATURE:
<223> OTHER INFORMATION: Synthetic targeting sequence

<400> SEQUENCE: 10
gagagtgtag ataaggtca                                                   19

<210> SEQ ID NO 11
<211> LENGTH: 19
<212> TYPE: DNA
<213> ORGANISM: Artificial Sequence
<220> FEATURE:
<223> OTHER INFORMATION: Synthetic targeting sequence

<400> SEQUENCE: 11
caatgttggt cttagtaaa                                                   19

<210> SEQ ID NO 12
<211> LENGTH: 19
<212> TYPE: DNA
<213> ORGANISM: Artificial Sequence
<220> FEATURE:
<223> OTHER INFORMATION: Synthetic targeting sequence

<400> SEQUENCE: 12
ctgagaagat tgctcacat                                                   19

<210> SEQ ID NO 13
<211> LENGTH: 19
<212> TYPE: DNA
<213> ORGANISM: Artificial Sequence
<220> FEATURE:
<223> OTHER INFORMATION: Synthetic targeting sequence

<400> SEQUENCE: 13
ttgggaagag tattacaaa                                                   19

<210> SEQ ID NO 14
<211> LENGTH: 19
<212> TYPE: DNA
<213> ORGANISM: Artificial Sequence
<220> FEATURE:
<223> OTHER INFORMATION: Synthetic targeting sequence

<400> SEQUENCE: 14
agcagattga ccatgcaaa                                                   19

<210> SEQ ID NO 15
<211> LENGTH: 20
<212> TYPE: DNA
<213> ORGANISM: Artificial Sequence
<220> FEATURE:
<223> OTHER INFORMATION: synthetic targeting sequence

<400> SEQUENCE: 15
gcatccagtt caagcaagat                                                  20

```
<210> SEQ ID NO 16
<211> LENGTH: 39
<212> TYPE: DNA
<213> ORGANISM: Artificial Sequence
<220> FEATURE:
<223> OTHER INFORMATION: Synthetic Primer

<400> SEQUENCE: 16
gggtcggagg cgagcggggc accgcaggct cgcaagcgg                              39

<210> SEQ ID NO 17
<211> LENGTH: 39
<212> TYPE: DNA
<213> ORGANISM: Artificial Sequence
<220> FEATURE:
<223> OTHER INFORMATION: Synthetic Primer

<400> SEQUENCE: 17
ccgcttgcga gcctgcggtg ccccgctcgc ctccgaccc                              39

<210> SEQ ID NO 18
<211> LENGTH: 37
<212> TYPE: DNA
<213> ORGANISM: Artificial Sequence
<220> FEATURE:
<223> OTHER INFORMATION: Synthetic Primer

<400> SEQUENCE: 18
cagcggctca cgcacctggc cccggaggag aaagcgc                                37

<210> SEQ ID NO 19
<211> LENGTH: 37
<212> TYPE: DNA
<213> ORGANISM: Artificial Sequence
<220> FEATURE:
<223> OTHER INFORMATION: Synthetic Primer

<400> SEQUENCE: 19
gcgctttctc ctccggggcc aggtgcgtga gccgctg                                37

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

<400> SEQUENCE: 20
acacgcttgg gaatggacac                                                   20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
ccatgggaag atgttctggg                                                   20

<210> SEQ ID NO 22
<211> LENGTH: 21
<212> TYPE: DNA
<213> ORGANISM: Artificial Sequence
<220> FEATURE:
<223> OTHER INFORMATION: Synthetic Primer
```

-continued

<400> SEQUENCE: 22
agtccctgcc ctttgtacac a                                    21

<210> SEQ ID NO 23
<211> LENGTH: 18
<212> TYPE: DNA
<213> ORGANISM: Artificial Sequence
<220> FEATURE:
<223> OTHER INFORMATION: Synthetic Primer

<400> SEQUENCE: 23
cgttccgagg gcctcact                                        18

<210> SEQ ID NO 24
<211> LENGTH: 22
<212> TYPE: DNA
<213> ORGANISM: Artificial Sequence
<220> FEATURE:
<223> OTHER INFORMATION: Synthetic Primer

<400> SEQUENCE: 24
ccccagtgtc aaactgtacc ag                                   22

<210> SEQ ID NO 25
<211> LENGTH: 24
<212> TYPE: DNA
<213> ORGANISM: Artificial Sequence
<220> FEATURE:
<223> OTHER INFORMATION: Synthetic Primer

<400> SEQUENCE: 25 agcgttttcca attttccata aatt                                24

<210> SEQ ID NO 26
<211> LENGTH: 19
<212> TYPE: DNA
<213> ORGANISM: Artificial Sequence
<220> FEATURE:
<223> OTHER INFORMATION: Synthetic Primer

<400> SEQUENCE: 26
tcatcggacg cacttggaa                                       19

<210> SEQ ID NO 27
<211> LENGTH: 21
<212> TYPE: DNA
<213> ORGANISM: Artificial Sequence
<220> FEATURE:
<223> OTHER INFORMATION: Synthetic Primer

<400> SEQUENCE: 27
caaccacctt gaatggcaag a                                    21

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer

<400> SEQUENCE: 28
ccggtgtttg aacgtcatct                                      20

<210> SEQ ID NO 29
<211> LENGTH: 20

```
<212> TYPE: DNA
<213> ORGANISM: Artificial Sequence
<220> FEATURE:
<223> OTHER INFORMATION: Synthetic Primer

<400> SEQUENCE: 29
caatgcctga caagactcca                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Primer

<400> SEQUENCE: 30
atcatctttg gtggccgtag                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Primer

<400> SEQUENCE: 31
atcttgccct tgtgttctgc                                              20

<210> SEQ ID NO 32
<211> LENGTH: 26
<212> TYPE: DNA
<213> ORGANISM: Artificial Sequence
<220> FEATURE:
<223> OTHER INFORMATION: Synthetic Primer

<400> SEQUENCE: 32
tgatgtgaat gacttggata cagaca                                       26

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33
caatgcctga caagactcca                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
gaaaagatca ttggcggaaa                                              20

<210> SEQ ID NO 35
<211> LENGTH: 23
<212> TYPE: DNA
<213> ORGANISM: Artificial Sequence
<220> FEATURE:
<223> OTHER INFORMATION: Synthetic Primer

<400> SEQUENCE: 35
cccagagtgc tcaggatgtt aag                                          23
```